United States Patent [19]

Brewster et al.

[11] Patent Number: 4,567,197

[45] Date of Patent: Jan. 28, 1986

[54] 1,3-DIOXAN-5-YLALKENOIC ACIDS

[75] Inventors: Andrew G. Brewster; Peter W. R. Caulkett, both of Macclesfield, United Kingdom

[73] Assignee: Imperial Chemical Industries PLC, London, England

[21] Appl. No.: 492,247

[22] Filed: May 6, 1983

[30] Foreign Application Priority Data

May 12, 1982 [GB] United Kingdom ............... 8213702

[51] Int. Cl.[4] .................. A61K 31/335; C07D 319/06
[52] U.S. Cl. .................................. 514/452; 549/373; 549/375
[58] Field of Search ................. 549/375, 373; 514/452

[56] References Cited

FOREIGN PATENT DOCUMENTS 0094239 11/1983 European Pat. Off. ............ 549/375
2046733 11/1980 United Kingdom ............... 549/373

OTHER PUBLICATIONS

J. Fried et al. in "Advances in Prostaglandin and Thromboxane Research", vol. 6, pp. 427–436, Raven Press, New York, 1980.

*Primary Examiner*—Ethel G. Love
*Attorney, Agent, or Firm*—Cushman, Darby & Cushman

[57] ABSTRACT

The invention concerns novel 4-phenyl-1,3-dioxan-5-ylalkenoic acid derivatives of the formula I having cis relative stereochemistry at positions 4 and 5 of the dioxane ring and wherein Ra and Rb are variously hydrogen, alkyl, halogenoalkyl, alkenyl, and optionally substituted aryl or arylalkyl, Rc is hydroxy, alkoxy or alkanesulphonamido, n is 1 or 2, A is ethylene or vinylene, Y is (2-5C)polymethylene optionally substituted by alkyl, and benzene ring B is optionally substituted phenyl, or, when Rc is hydroxy, a salt thereof. The acid derivatives antagonize one or more of the actions of thromboxane $A_2$ ($TXA_2$) and are expected to be of value in those disease conditions in which $TXA_2$ is involved. The invention also provides pharmaceutical compositions containing an acid derivative of formula I, and processes for their chemical production.

15 Claims, No Drawings

1,3-DIOXAN-5-YLALKENOIC ACIDS

This invention relates to novel 1,3-dioxan-5-ylalkenoic acids and their derivatives, which antagonise one or more of the actions of thromboxane $A_2$ (hereafter referred to as "$TXA_2$"), and are valuable therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction and angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

Certain 4-substituted-1,3-dioxan-trans-5-ylalkenoic acids typified by the compound of the formula A [set out, together with the other structural formulae referred to herein, on the accompanying formulae sheets] are known (UK patent application No. 8004647, published as Ser. No. 2046733A) as inhibitors of the enzyme responsible for the synthesis of $TXA_2$. Similarly, certain 6-alkynyl-1,3-dioxan-cis-4-ylalkenoic acids typified by the compound of the formula B are known (Fried *et alia*, *Adv. Prostaglandin and Thromboxane Research*, 1980, 6, 427–436) to inhibit various enzymes in the arachidonic acid cascade. However, neither of these groups of 1,3-dioxanylalkenoic acids has been described as having any antagonist action against the effects of $TXA_2$.

We have now discovered that the novel, chemically distinct 4-substituted-1,3-dioxan-5-ylalkenoic acids and their derivatives, of formula I below, unexpectedly possess the property of antagonising one or more of the actions of $TXA_2$ and this is the basis for our invention.

According to the invention there is provided a 4-phenyl-1,3-dioxan-cis-5-ylalkenoic acid derivative of the formula I wherein Ra and Rb are independently hydrogen, (2–6C)alkenyl, (1–8C)alkyl optionally bearing up to three halogeno substituents, pentafluorophenyl, aryl or aryl-(1–4C)alkyl, the latter two of which may optionally bear up to three substituents selected from halogeno, (1–6C)alkyl, (1–6C)alkoxy, (1–4C)alkylenedioxy, trifluoromethyl, cyano, nitro, hydroxy, (2–6C)alkanoyloxy, (1–6C)alkylthio, (1–6C)alkanesulphonyl, (1–6C)alkanoylamino, and oxapolymethylene of 2 to 4 carbon atoms, provided that when both Ra and Rb are alkyl or alkenyl, the total number of carbon atoms in Ra and Rb taken together is 8 or less; or Ra and Rb together form polymethylene of 2 to 7 carbon atoms, optionally bearing one or two (1–4C)alkyl substituents; Rc is hydroxy, (1–6C)alkoxy or (1–6C)alkanesulphonamido; n is the integer 1 or 2; A is ethylene or vinylene; Y is polymethylene of 2 to 5 carbon atoms optionally bearing (1–4C)alkyl as a substituent; benzene ring B optionally bears one or two substituents selected from halogeno, (1–6C)alkyl, (1–6C)alkoxy, hydroxy, (2–6C)alkanoyloxy, (1–6C)alkanoylamino, trifluoromethyl and nitro; and the substituents at positions 4 and 5 of the dioxane ring have cis-relative stereochemistry; or for those compounds wherein Rc is hydroxy, a salt thereof with a base affording a physiologically acceptable cation.

It will be appreciated that the compounds of formula I contain at least two asymmetric carbon atoms (i.e. at $C_4$ and $C_5$ of the dioxane ring) and may exist and be isolated in racemic and optically active forms. In addition those compounds of formula I wherein A is vinylene exist, and may be isolated, in separate stereoisomeric forms ('E' and 'Z') about that group. It is to be understood that the present invention encompasses any racemic, optically active or stereoisomeric form (or mixtures thereof) which is capable of antagonising one or more of the actions of $TXA_2$, it being well known in the art how to prepare individual optical isomers (for example by synthesis from optically active starting materials or resolution of a racemic form) and individual 'E' and 'Z' stereoisomers (for example by chromatographic separation of a mixture thereof), and how to determine the $TXA_2$ antagonist properties using the standard test described hereafter.

In this specification, the terms Ra, Rb and Rc etc, are used to depict generic radicals and have no other significance.

A particular value for Ra or Rb when it is (1–8C)alkyl is, for example, methyl, ethyl, propyl, isopropyl, butyl, pentyl, hexyl, heptyl or octyl, and when it is (1–8C)alkyl bearing up to three halogeno atoms is, for example chloromethyl, 2-chloroethyl, trifluoromethyl or 2,2,2-trifluoroethyl.

A particular value for Ra or Rb when it is aryl is, for example, phenyl, 1-naphthyl or 2-naphthyl; when it is aryl-(1–4C)alkyl is, for example, benzyl, 1-phenylethyl or 2-phenylethyl; and when it is (2–6C)alkenyl is, for example, vinyl, allyl or 2-methylallyl.

Particular values for optional substituents, which may be present on benzene ring B or on an aromatic moiety which constitutes or is part of Ra or Rb as defined above, are, for example:

for halogeno: fluoro, chloro, bromo or iodo;
for (1–6C)alkyl: methyl, ethyl, propyl or isopropyl;
for (1–6C)alkoxy: methoxy, ethoxy or propoxy;
for (1–4C)alkylenedioxy: methylenedioxy, ethylenedioxy or isopropylidenedioxy;
for (1–6C)alkylthio: methylthio or ethylthio;
for (1–6C)alkanesulphonyl: methanesulphonyl or ethanesulphonyl;
for (1–6C)alkanoylamino: formamido, acetamido or propionamido;
for (2–6C)alkanoyloxy: acetoxy or propionyloxy; and
for oxapolymethylene of 2 to 4 carbon atoms, a group of the formula $-CH_2OCH_2-$ or $-CH_2CH_2OCH_2-$.

In general when one of Ra and Rb is hydrogen it is preferred that the other of Ra and Rb is arranged so as to have cis-relative stereochemistry with reference to the substituents at positions 4 and 5 of the dioxane ring.

A particular value for Ra and Rb when together they form polymethylene of 2 to 7 carbon atoms is, for example, ethylene, trimethylene, tetramethylene, pentamethylene or hexamethylene; and a particular value for an optional (1–4C)alkyl substituent thereon is, for example, methyl.

A particular value for Rc when it is (1–6C)alkanesulphonamido is, for example, methanesulphonamido, ethanesulphonamido, propanesulphonamido or 1-methylethanesulphonamido.

A particular value for Rc when it is (1–6C)alkoxy is, for example, methoxy or ethoxy.

A particular value for Y is, for example, ethylene, trimethylene or tetramethylene; and a particular value for an optional substituent thereon is, for example, methyl.

Specific examples of Ra and Rb are, for example, hydrogen, methyl, ethyl, propyl, isopropyl, butyl, pentyl, hexyl, octyl, vinyl, allyl, 2-methylallyl, trifluoromethyl, chloromethyl, 2-chloroethyl, phenyl optionally bearing a fluoro, chloro, bromo, methyl, methoxy, trifluoromethyl, methylthio, methanesulphonyl, nitro, hydroxy, cyano, acetamido, methylenedioxy or a methyleneoxymethylene (—CH$_2$OCH$_2$—) substituent, dichlorophenyl, dimethylphenyl, pentafluorophenyl, 1-naphthyl, 2-naphthyl or benzyl; or are, for example, when they together form trimethylene, pentamethylene or hexamethylene, optionally bearing a methyl substituent.

Specific values for benzene ring B are, for example, when it is phenyl, 2-methylphenyl, 2-ethylphenyl, 2-isopropylphenyl, 2-methoxyphenyl, 2-fluorophenyl, 2-chlorophenyl, 2-bromophenyl, 2-hydroxyphenyl, 2-trifluoromethylphenyl, 3-trifluoromethylphenyl, 3-fluorophenyl, 3-chlorophenyl, 4-fluorophenyl, 4-methylphenyl or 2,6-difluorophenyl.

A preferred value for Rc is, for example, hydroxy, methoxy, ethoxy, methanesulphonamido or ethanesulphonamido, of which hydroxy is especially preferred.

A preferred value for A is vinylene, and for Y is, for example, trimethylene. A preferred value for n is the integer 1.

In general when A is vinylene it is preferred that the adjacent carbon atoms have cis-relative stereochemistry i.e. the 'Z' configuration.

A preferred value for benzene ring B is, for example, when it is unsubstituted; ortho-substituted by fluoro, chloro, methyl, hydroxy, methoxy, ethyl or isopropyl; or meta-substituted by fluoro or chloro.

A preferred group of acid derivatives of the invention comprises those compounds of formula Ia wherein Ra and Rb are:

(i) independently hydrogen or (1–4C)alkyl, optionally bearing 1 to 3 halogeno substituents;

(ii) one of the two is hydrogen or (1–4C)alkyl, and the other is phenyl, naphthyl or phenyl-(1–4C)alkyl, optionally bearing 1 or 2 substituents selected from halogeno, (1–4C)alkyl, (1–4C)alkoxy, (1–4C)alkylenedioxy, trifluoromethyl, cyano, nitro, hydroxy, (2–4C)alkanoyloxy, (1–4C)alkylthio, (1–4C)alkanesulphonyl, (1–4C)alkanoylamino and oxapolymethylene of 2 to 4 carbon atoms, or pentafluorophenyl;

(iii) one of the two is hydrogen and the other is (5–8C)alkyl or (2–6C)alkenyl; or (iv) both together form polymethylene of 2 to 7 carbon atoms optionally bearing a (1–4C)alkyl substituent;

Rc is hydroxy, (1–4C)alkoxy or (1–4C)alkanesulphonamido; and benzene ring B optionally bears a single substituent located at the 2-position selected from halogeno, (1–4C)alkyl, (1–4C)alkoxy, hydroxy, (2–4C)alkanoyloxy, (1–4C)alkanoylamino and trifluoromethyl, or bears a 3-halogeno substituent; and the substituents at positions 4 and 5 of the dioxane ring have cis-relative stereochemistry; or for those compounds wherein Rc is hydroxy, a salt thereof with a base affording a physiologically acceptable cation.

Particular values for the various substituents in the above preferred group are, for example:
for (1–4C)alkyl: methyl, ethyl, propyl, isopropyl or butyl;
for (5–8C)alkyl: pentyl, hexyl, heptyl or octyl;
for (1–4C)alkoxy: methoxy or ethoxy;
for (1–4C)alkyl bearing 1 to 3 halogeno substituents: chloromethyl, 2-chloroethyl, 2,2,2-trifluoroethyl or trifluoromethyl;
for phenyl-(1–4C)alkyl: benzyl, 2-phenylethyl or 1-phenylethyl;
for halogeno: fluoro, chloro or bromo:
for (1–4C)alkylenedioxy: methylenedioxy, ethylenedioxy or isopropylidenedioxy;
for (2–4C)alkanoyloxy: acetoxy or propionyloxy;
for (1–4C)alkylthio: methylthio or ethylthio;
for (1–4C)alkanesulphonyl: methanesulphonyl or ethanesulphonyl;
for (1–4C)alkanoylamino: acetamido or propionamido; and
for oxapolymethylene of 2 to 4 carbon atoms: methyleneoxymethylene (—CH$_2$OCH$_2$) or ethyleneoxy (—CH$_2$CH$_2$O—).

Specific combinations of Ra and Rb which are preferred are, by way of example:

(i) Ra and Rb are both hydrogen, methyl, ethyl, propyl, butyl or trifluoromethyl;

(ii) one of Ra is hydrogen and the other is trifluoromethyl, chloromethyl, benzyl, isopropyl, hexyl, octyl, phenyl (optionally bearing 1 or 2 fluoro, chloro, bromo, methyl, methoxy, trifluoromethyl, hydroxy, cyano, methylthio or acetamido), phenyl bearing methylenedioxy or methyleneoxymethylene (—CH$_2$OCH$_2$—), pentafluorophenyl, 1-naphthyl or 2-naphthyl; and (iii) Ra and Rb together form trimethylene, tetramethylene, pentamethylene, hexamethylene or a group of the formula: —CH$_2$CH$_2$.CHCH$_3$.CH$_2$CH$_2$—.

Specific preferred values for Ra or Rb when it is a mono or disubstituted phenyl are, for example, 2-fluoro-, 3-fluoro-, 4-fluoro-, 2-chloro-, 3-chloro-, 4-chloro-, 2-bromo-, 3-bromo-, 4-bromo-, 2-methyl-, 3-methyl-, 4-methyl-, 2-methoxy-, 3-methoxy-, 4-methoxy-, 2-trifluoromethyl-, 3-trifluoromethyl-, 4-trifluoromethyl-, 3-hydroxy-, 4-cyano-, 4-methylthio-, 4-acetamido-, 3,4-dichloro-, 2,4-dimethyl-, 3,4-methylenedioxy- and 3,4-(methyleneoxymethylene)-phenyl.

Specific preferred values for benzene ring B are, for example, when it is phenyl, or 2-fluoro-, 2-chloro-, 2-bromo-, 2-methyl-, 2-ethyl-, 2-isopropyl-, 2-methoxy-, 2-hydroxy-, 3-fluoro- or 3-chloro-phenyl.

A further preferred group of acids of the invention comprises compounds of the formula Ib wherein :

(i) Ra and Rb are both hydrogen, methyl, ethyl, propyl, butyl, or trifluoromethyl;

(ii) or together form trimethylene, tetramethylene, pentamethylene, hexamethylene or a group of the formula: —CH$_2$CH$_2$.CHCH$_3$.CH$_2$CH$_2$—; or (iii) Ra is (3–8C)alkyl, trifluoromethyl, chloromethyl, 2-chloroethyl, pentafluorophenyl, or phenyl, benzyl or naphthyl, the last three of which may optionally bear 1 or 2 halogeno, (1–4C)alkyl, (1–4C)alkoxy, trifluoromethyl, hydroxy, cyano, (1–4C)alkylthio or (1–4C)alkanoylamino substituents, or a methylenedioxy or methyleneoxymethylene substituent, and Rb is hydrogen;

benzene ring B is unsubstituted or is 2-halogeno-, 2-(1-4C)alkyl-, 2-(1-4C)alkoxy-, 2-hydroxyor- or 3-halogeno-phenyl;

Ra and the substituents at the 4 and 5-positions of the dioxane ring have cis-relative stereochemistry; and the carbon atoms adjacent to the vinylene group have the indicated cis-relative stereochemistry; or a salt thereof with a base affording a physiologically acceptable cation; or a methyl or ethyl ester thereof; or a methanesulphonamido, ethanesulphonamido or 1-methylethanesulphonamido derivative thereof.

A preferred value for Ra when it is (3-8C)alkyl is, for example, isopropyl, butyl, hexyl or octyl.

Preferred values for substituents on Ra when it is phenyl, benzyl or naphthyl are, for example:
for halogeno: fluoro, chloro or bromo;
for (1-4C)alkyl: methyl;
for (1-4C)alkoxy: methoxy;
for (1-4C)alkylthio: methylthio; and
for (1-4C)alkanoylamino: acetamido.

Preferred values for substituents on benzene ring B are, for example:
for 2-halogeno: 2-fluoro, 2-chloro or 2-bromo;
for 3-halogeno: 3-fluoro or 3-chloro;
for 2-(1-4C)alkyl: 2-methyl, 2-ethyl or 2-isopropyl; and
for 2-(1-4C)alkoxy: 2-methoxy.

Particular salts of compounds of formula I wherein Rc is hydroxy are, for example, alkali metal and alkaline earth metal salts such as lithium, sodium, potassium, magnesium and calcium salts, aluminium and ammonium salts, and salts with organic amines or quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Specific compounds of the invention are described in the accompanying Examples and of these a compound of particular interest is 5(Z)-7-(2,2-diethyl-4-phenyl-1,3-dioxan-cis-5-yl)heptenoic acid or a pharmaceutically acceptable salt thereof.

The compounds of formula I may be manufactured by conventional procedures of organic chemistry well known in the art for the production of analogous compounds. Such processes are provided as a further feature of the invention and are illustrated by the following preferred procedures in which Ra, Rb, Rc, benzene ring B, n, A and Y have any of the meanings defined hereinbefore:

(a) For a compound wherein Rc is hydroxy and A is vinylene, reacting an aldehyde of the formula II with a Wittig reagent of the formula:

$$(Rd)_3P=CH.Y.CO_2^- M^+ \quad\quad III$$

wherein Rd is (1-6C)alkyl (especially methyl or ethyl) or aryl (especially phenyl), and M+ is, for example, an alkali metal cation such as the lithium, sodium or potassium cation.

The process in general produces compounds of formula I in which the carbon atoms adjacent to the vinylene have predominantly cis-relative stereochemistry i.e. the "Z" isomer. However the compounds of formula I having trans-relative stereochemistry (i.e. the "E" isomer) are also formed in the process and may be obtained by conventional separation of the mixture of "Z"- and "E"- isomers first obtained.

The process is conveniently performed in a suitable solvent or diluent, for example an aromatic solvent such as benzene, toluene or chlorobenzene, an ether such as 1,2-dimethoxyethane, dibutyl ether, tetrahydrofuran, dimethyl sulphoxide or tetramethylene sulphone, or in a mixture of one or more such solvents or diluents. The process is generally performed at a temperature in the range, for example, −80° C. to 40° C. but is conveniently performed at or near room temperature, that is in the range 15° to 35° C.

If desired the proportion of the product of the process with trans- relative stereochemistry about the double bond may frequently be increased by choice of a suitable solvent, for example tetramethylene sulphone, and/or addition of an alkali halide, for example lithium bromide, to the reaction mixture.

The starting Wittig reagents of formula III are in general well known in the art or may be obtained by analogous procedures. They are generally formed by treatment of the corresponding phosphonium halides with a strong base such as sodium hydride, lithium diisopropylamide, potassium t-butoxide or butyl lithium in a suitable solvent such as that used for the process itself, and are generally formed in situ immediately prior to carrying out process (a).

The starting materials of formula II may be obtained by the sequences shown in Schemes 1 or 2, (attached hereafter, many of which are illustrated in the accompanying Examples).

SCHEME I

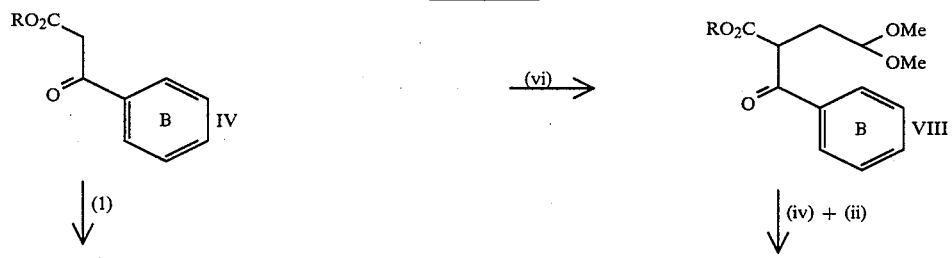

-continued
SCHEME I

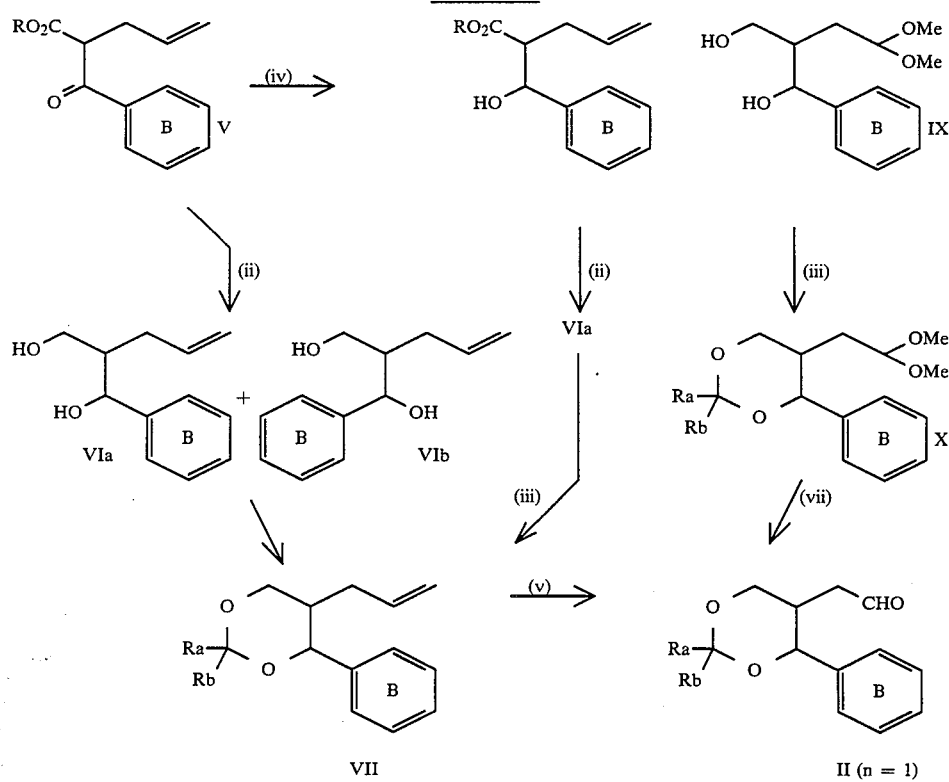

Reagents:
(i) NaOEt, EtOH, allyl bromide
(ii) LiAlH₄ or LiBH₄, THF
(iii) p-TsOH, RaRb.CO or RaRb.C(OMe)₂
(iv) Zn(BH)₂, Et₂O
(v) O₃, CH₂Cl₂, then Ph₃P; or OsO₄, NaIO₄, t-BuOH, H₂O
(vi) NaH, DMSO, BrCH₂CH(OMe)₂
(vii) H⁺, H₂O
Notes:
R = (1–4C)alkyl, for example Me or Et.

SCHEME II

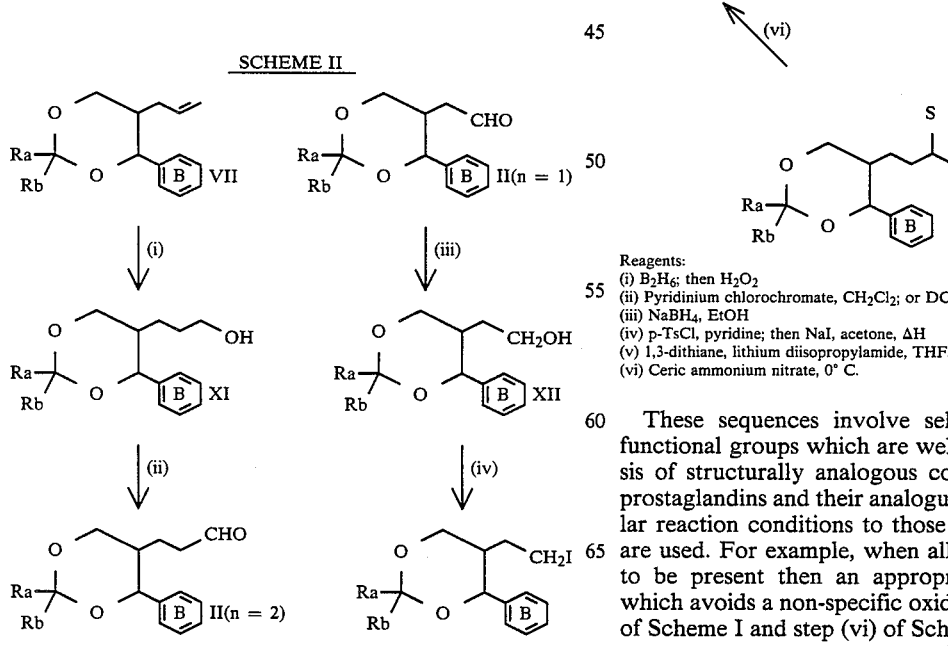

Reagents:
(i) B₂H₆; then H₂O₂
(ii) Pyridinium chlorochromate, CH₂Cl₂; or DCCI, DMSO, pyridine, TFA
(iii) NaBH₄, EtOH
(iv) p-TsCl, pyridine; then NaI, acetone, ΔH
(v) 1,3-dithiane, lithium diisopropylamide, THF, −78° C.
(vi) Ceric ammonium nitrate, 0° C.

These sequences involve selective conversions of functional groups which are well known in the synthesis of structurally analogous compounds, such as the prostaglandins and their analogues and, in general, similar reaction conditions to those well known in the art are used. For example, when alkylthio substituents are to be present then an appropriate sequence is used which avoids a non-specific oxidation step (e.g. step (v) of Scheme I and step (vi) of Scheme 2. Similarly, when a hydroxy substituent is to be present on benzene ring B then a starting material of formula IV may be used in which the hydroxy substituent has been protected for example as its trimethylsilyl ether). The protecting group is then removed, for example by reaction with tetrabutylammonium fluoride, in a conventional manner as a final step prior to carrying out process (a). Similarly, when an acyloxy substituent is to be present on benzene ring B, this may be produced by acylation of the corresponding hydroxy derivative of formula II using a conventional procedure as a final step.

It will be seen that a mixture of stereoisomers at positions 4,5 of the dioxane rings is generally obtained from Scheme 1 and that it is necessary to separate out the required cis-stereoisomer, conveniently after cyclisation of the 5-allyl-1,3-dioxanes VII, using a conventional procedure such as chromatography.

The 5-allyl-1,3-dioxanes VII may also be obtained by an acetal exchange reaction analogous to that described in process (b), for example by reacting [4,5-cis]-5-allyl-2,2-dimethyl-4-phenyl-1,3-dioxane with an excess of the appropriate ketone or aldehyde of the formula RaRb.CO (or its dimethyl acetal or ketal) in the presence of p-toluenesulphonic acid. This procedure and related alternatives are described in the accompanying Examples.

The keto esters IV may be obtained by conventional organic syntheses as illustrated in the accompanying Examples.

(b) Reacting an erythro-diol derivative of the formula XIII wherein one of Qa and Qb is hydrogen and the other is hydrogen, alkanesulphonyl, arenesulphonyl or a group of the formula —$CRR^1$.OH wherein R and $R^1$ are the same or different alkyl, with a carbonyl compound of the formula RaRb.CO, or an acetal, hemiacetal or hydrate thereof.

A suitable value for Qa or Qb when it is alkanesulphonyl is, for example, methanesulphonyl or ethanesulphonyl and when it is arenesulphonyl is, for example, benzenesulphonyl or p-toluenesulphonyl. A suitable value for R or $R^1$ is, for example, methyl or ethyl.

The carbonyl compound of the formula RaRb.CO (or its hydrate, or its acetal or hemiacetal with a (1–4C)alkanol) is preferably used in excess.

Depending on the nature of Qa and Qb different reaction conditions are necessary. Thus, when Qa and Qb are both hydrogen or when one is a group of the formula —$CRR^1$.OH and the other is hydrogen, the reaction is carried out in the presence of an acid catalyst, for example, hydrogen chloride, hydrogen bromide, sulphuric acid, phosphoric acid, p-toluenesulphonic acid or the anionic form of a sulphonated polystyrene catalyst, conveniently in a suitable solvent or diluent, for example an ether such as diethyl ether, dibutyl ether, 1,2-dimethoxyethane or tetrahydrofuran, and at a temperature in the range, for example, 10° to 120° C. The acid catalyst may also be provided by the inherent acidity of the starting material of formula XIII wherein Rc is hydroxy, as illustrated in Example 8 hereafter.

Similarly, when one of Qa and Qb is alkanesulphonyl or arenesulphonyl and the other is hydrogen, the reaction is carried out first in the presence of an acid catalyst, for example under the conditions described above to produce an intermediate of the formula XIII, wherein one of Qa and Qb is alkanesulphonyl or arenesulphonyl, and the other is a group of the formula —CRaRb.OH. The latter intermediate may then be cyclised in situ to the required compound of formula I by addition of a strong base, for example, sodium hydride or butyl lithium, in a suitable solvent or diluent, for example in the ether solvent used for the acid catalysed step above, and at a temperature in the range, for example, 30°–100° C.

It will be appreciated that the above mentioned intermediate may also be isolated, characterised and separately cyclised under the influence of strong base to give a compound of formula I. Such a procedure is encompassed by the invention.

Those starting materials of formula XIII wherein Qa and Qb are both hydrogen (that is an erythrodiol of formula XIII) may be obtained by mild hydrolysis or alcoholysis of the dioxane ring of a compound of formula I, for example, in which Ra and Rb are both methyl or ethyl radicals, obtained by another process described herein. This reaction will normally be carried out at a temperature in the range, for example, 25°–100° C. and preferably in the range 30°–60° C., using an aqueous mineral acid such as hydrochloric acid in an alcoholic solvent such as ethanol or 2-propanol. Those starting materials of formula XIII wherein one of Qa and Qb is a group of the formula —$CRR^1$.OH and the other is hydrogen, are generally obtained as intermediates in the above mentioned formation of the erythrodiol of formula XIII (Qa=Qb=H) and are not normally isolated or characterised. Accordingly, the invention also provides a process which comprises reacting a compound of formula I for example wherein Ra and Rb are methyl or ethyl, with an excess of a compound of the formula RaRb.CO in the presence of an acid-catalyst (such as those mentioned above), conveniently in a suitable solvent or diluent (such as an ether mentioned above) and at a temperature in the range for example 10° to 120° C.

Those starting materials of formula XIII wherein one Qa and Qb is alkanesulphonyl or arenesulphonyl and the other is hydrogen, may be obtained from the corresponding erythro- diol of formula XIII (Qa=Qb=H) by reaction with one molecular equivalent of the appropriate alkanesulphonyl or arenesulphonyl halide, for example methanesulphonyl chloride or p-toluenesulphonyl chloride, in a suitable solvent or diluent (such as an ether or dichloromethane) and in the presence of a base such as pyridine or triethylamine.

The erythro-diols of formula XIII (Qa=Qb=H A= vinylene, Rc=OH) may alternatively be obtained by carrying out the Wittig reaction in process (a) hereinbefore using a trimethylsilylated aldehyde of the formula XIV (itself prepared, for example, by replacing step (iii) in Scheme 1 by a conventional silylation procedure) and then removing the trimethylsilyl protecting groups in a conventional manner, for example with tetrabutylammonium fluoride, from the Wittig reaction product of the formula XV. When a starting material of formula XIII wherein Rc is other than hydroxy is required, the carboxylic acid group of the Wittig reaction product XV may be derivatised by the procedures described hereinafter, prior to the removal of the trimethylsilyl protecting groups.

The starting materials of formula XIII wherein A is ethylene may be obtained by conventional hydrogenation of the corresponding compounds wherein A is vinylene.

Process (b) is not normally suitable for the production of compounds of formula I wherein both Ra and Rb are trifluoromethyl.

Under some circumstances when Rc is hydroxy in the starting materials of formula XIII, some degree of concomitant esterification may occur during process (b) (see Example 83 hereafter), such that hydrolysis [according to process (d) hereafter] of the reaction product may be necessary in order to obtain the required compound of formula I wherein Rc is hydroxy.

The necessary starting ketones of formula RaRb.CO and their derivatives are generally already known or may readily be obtained by standard techniques of organic chemistry.

(c) For a compound of formula I wherein Rc is hydroxy, oxidising an alcohol of the formula XVI.

A range of oxidising agents is suitable for use in this process, for example, chromium trioxide in aqueous sulphuric acid and acetone; platinum and oxygen in aqueous acetone or tetrahydrofuran; or alkaline persulphate in the presence of ruthenium trichloride. A suitable solvent or diluent which is compatible with the oxidising agent may conveniently be employed.

The process may be carried out at a temperature in the range, for example 10° to 50° C., but is preferably performed at or near room temperature in order to minimise the risk of oxidation of other sensitive substituents in the molecule. Equally, where such substituents are present, the process may be conveniently performed in two steps using two oxidising agents, that is by intermediate formation of the corresponding aldehyde of the formula XVII using an oxidising agent such as pyridinium chlorochromate (preferably in a solvent such as dichloromethane), or the Pfitzner-Moffatt reagent (dicyclohexylcarbodiimide and dimethyl sulphoxide in the presence of an acid catalyst for example pyridine trifluoroacetate), in both cases at or near room temperature. The aldehyde of formula XVII may then be separately oxidised to the required carboxylic acid of formula I (Rc=OH) by reaction with a mild oxidising agent such as silver oxide in the presence of an alkali metal hydride such as sodium hydroxide, conveniently in a solvent or diluent, for example a (1-4C)alkanol such as ethanol, and at or near room temperature. This latter process is also provided as a feature of the invention.

The starting materials of formula XVI wherein A is a vinylene radical may be obtained by analogy with process (a) but using a Wittig reagent of the formula:

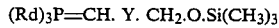

(Rd)$_3$P=CH.Y.CH$_2$.O.Si(CH$_3$)$_3$ (wherein Rd has the meaning defined previously) and an aldehyde of formula II and then removing the trimethylsilyl protecting group in a conventional manner from the product to give the required alcohol of formula XVI. Similarly those starting materials of formula XVI wherein A is ethylene may be obtained by conventional hydrogenation of the corresponding compounds of formula XVI wherein A is vinylene.

(d) For a compound of formula I wherein Rc is hydroxy, hydrolysing a compound of the formula XVIII wherein W is alkoxycarbonyl, phenoxycarbonyl, benzyloxycarbonyl, cyano or carbamoyl.

A particular value for W when it is alkoxycarbonyl is methoxycarbonyl or ethoxycarbonyl.

The hydrolysis is conveniently carried out under the influence of base, for example an alkali metal hydroxide (such as sodium or potassium hydroxide) in a suitable aqueous solvent, for example a (1-4C)alkanol (such as methanol or ethanol) or a glycol (such as ethylene glycol) at a temperature in the range, for example, 15° to 150° C. In general, higher reaction temperatures are required when W is cyano or carbamoyl, for example in the range 80°-150° C.

The starting materials of formula XVIII wherein W is cyano may be obtained by reaction of an alcohol of the formula XIX with methanesulphonyl chloride in a suitable solvent such as dichloromethane in the presence of a base such as triethylamine to give the mesylate of the formula XX, which is then reacted with potassium cyanide in dimethyl sulphoxide at 50°-100° C. The starting alcohols of formula XIX may themselves be obtained by analogy with those of formula XVI in process (c) hereinbefore by using a Wittig reagent of the formula:

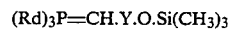

(Rd)$_3$P=CH.Y.O.Si(CH$_3$)$_3$ wherein Rd has the meaning defined previously. When A is ethylene the alcohol of formula XIX may be hydrogenated prior to reaction with methanesulphonyl chloride.

The necessary starting materials of formula XVIII may be obtained by analogy with other processes described herein.

(e) For a compound of formula I wherein Ra, Rb or benzene ring B bears a hydroxy substituent, deprotecting a corresponding derivative of said compound wherein the hydroxy substituent is protected by a trimethylsilyl, (1-6C)alkyl (such as methyl or ethyl) or acyl (such as acetoxy or benzoyloxy) protecting group.

The deprotection conditions required necessarily depend on the protecting groups concerned. Thus, for example, when it is methyl or ethyl (i.e. the starting material is the corresponding methoxy or ethoxy compound of formula I) the deprotection may be carried out, for example, by heating with sodium thioethoxide in a suitable solvent (such as N,N-dimethylformamide) at an elevated temperature, for example 90°-160° C. Similarly, when the protecting group is acyloxy, it may be removed, for example by hydrolysis in the presence of a base (such as sodium or potassium hydroxide) in a suitable aqueous solvent [such as a (1-4C)alkanol or a glycol] at a temperature in the range, for example, 10°-60° C. Similarly in the case of a trimethylsilyl protecting group, it may be removed for example, by reaction with aqueous tetrabutylammonium fluoride or sodium fluoride in conventional manner.

The necessary protected derivatives of the formula I compounds may be made by analogy with the other processes described herein.

(f) For a compound of formula I wherein Ra and Rb are both hydrogen, reacting an erythro-diol of the formula XIII wherein Qa and Qb are both hydrogen, with methylene bromide in the presence of base.

A particularly suitable base is for example, sodium or potassium hydroxide, or sodium hydride.

The process is preferably carried out in a suitable solvent or diluent, for example dimethyl sulphoxide, and at a temperature in the range, for example, 10° to 40° C., conveniently at or near room temperature.

When a compound of formula I wherein Rc is (1-6C)alkoxy is required, the corresponding acid of formula I wherein Rc is hydroxy, or a reactive derivative thereof, is esterified using a conventional procedure.

Thus, for example, an acid of formula I wherein Rc is hydroxy, or a reactive derivative thereof, L may be esterified by reaction with the appropriate (1-6C)alkanol.

It will be appreciated that when a free acid of formula I is used in the process, water is produced during the reaction. Consequently, in such cases it is particularly convenient to perform the process in the presence of a suitable dehydrating agent, for example dicyclohexylcarbodiimide, in the presence of a suitable solvent or diluent for example tetrahydrofuran, acetone, methylene chloride or 1,2-dimethoxyethane, at a temperature in the range, for example, 10° to 50° C., but preferably at or near room temperature.

A suitable reactive derivative of an acid of formula I is, for example, an acid chloride, bromide, anhydride, mixed anhydride with formic acid, or an azide, which may be produced from the free acid in conventional manner. When such a derivative is used in the process, no additional dehydrating agent is necessary, and the (1-6C)alkanol is conveniently used in large excess, optionally diluted with a suitable diluent or solvent such as an ether, for example tetrahydrofuran or 1,2-dimethoxyethane.

In general, when a reactive derivative of an acid of formula I is used no external heating of the reaction is necessary.

When a compound of formula I wherein Rc is (1-6C)alkanesulphonamido is required, the corresponding acid of formula I wherein Rc is hydroxy, or a reactive derivative thereof, is reacted with the appropriate (1-6C)alkanesulphonamide.

Thus, for example a free acid of formula I wherein Rc is hydroxy may be reacted with a suitable dehydrating agent, for example dicyclohexylcarbodiimide, optionally together with an organic base, for example 4-dimethylaminopyridine, in the presence of a suitable solvent or diluent, for example methylene chloride at a temperature in the range, 10° to 50° C., but preferably at or near room temperature. Alternatively, a reactive derivative of an acid of formula I, wherein Rc is hydroxy, for example an acid halide (such as the acid chloride) may be reacted with an alkali metal salt (such as the sodium salt) of the appropriate (1-6C)alkanesulphonamide, conveniently at or near room temperature and in a suitable solvent or diluent, for example an ether, N,N-dimethylformamide or methylene chloride.

When a compound of formula I wherein A is ethylene is required, the corresponding compound of formula I wherein A is vinylene is hydrogenated, in the presence of a catalyst.

The hydrogenation may be carried out in a suitable solvent or diluent, for example a (1-4C)alkanol (such as ethanol or 2-propanol), optionally in the presence of water, and at a temperature in the range, for example, 15° to 35° C., using hydrogen at a pressure of, for example, 1 to 2 atmospheres.

A suitable catalyst is, for example, a noble metal catalyst such as palladium metal conveniently on an inert support such as carbon, barium sulphate or barium carbonate.

When a salt of a compound of formula I wherein Rc is hydroxy is required, it is obtained by reaction with the appropriate base affording a physiologically acceptable cation, or by any other conventional procedure.

Further, when an optically active form of a compound of formula I is required, one of the aforesaid processes is carried out using an optically active starting material. Alternatively, when Rc is hydroxy, a racemic form of the said compound may be reacted with an optically active form of a suitable organic base, for example ephedrine, N,N,N-trimethyl (1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

When an optically active form of a compound of formula I wherein Rc is other than hydroxy is required, it may be obtained using the aforementioned esterification or amidification procedures using the appropriate optically active form of said acid.

The intermediates of formula II and VII as defined hereinbefore are novel and are provided as further separate features of the invention.

As stated earlier, the compounds of formula I are antagonists of one or more of the actions of $TXA_2$, for example certain of its actions on blood platelets, the vasculature and/or the lung. The antagonism may be demonstrated in one or other of the following tests:

(a) The standard rabbit aortal strip model devised by Piper and Vane (*Nature*, 1969, 223, 29-35) using as agonist a freshly prepared sample of $TXA_2$, generated by addition of arachidonic acid (25 μg. to citrated, platelet rich rabbit plasma (250 μl.) and allowing the mixture to aggregate fully over 90 seconds before use;

(b) a standard blood platelet aggregation test based on that described by Born (*Nature*, 1962, 194, 927-929) and involving measuring the inhibition by a test compound of aggregation of citrated, platelet rich human plasma induced by a sub-maximal concentration (in the range 25-100 μg/ml.) of arachidonic acid; and (c) a standard bronchoconstriction test involving measuring the inhibition by a test compound of the bronchoconstriction induced in the Konzett-Rossler guinea-pig model (as modified by Collier and James, *Brit. J. Pharmacol.*, 1967, 30, 283-307) by intravenous administration of the $TXA_2$ mimetic agent, U46619 at 1-1.5 μg/kg.

By way of illustration only, the compound of the formula I, 5(Z)-7-(2,2-dimethyl-4-phenyl-1,3-dioxan-cis-5-yl)heptenoic acid possessed the following properties in the above tests:

(a) $pA_2$ 6.28;
(b) $IC_{50}$ ca $6.7 \times 10^{-5}$M; and
(c) 90% reduction of bronchoconstriction at 5 mg./kg. i.v. In general, other compounds of formula I show similar or better levels of activity in test (a) [$pA_2$ 5.0], and in at least one of tests (b) and (c) without any signs of overt toxicity at the active dose in test (c).

Similarly, the following representative group of acids of formula Ib show significant activity in test (a) [$pA_2 \geq 5.9$] and oral activity at 50 mg./kg. (or much less) in test (c) without any signs of overt toxicity:

| Compound | Ra | Rb | Benzene Ring B |
| --- | --- | --- | --- |
| 1 | Ethyl | Ethyl | Phenyl |
| 2 | Pentamethylene | | Phenyl |
| 3 | Methyl | Methyl | 3-Fluorophenyl |
| 4 | Methyl | Methyl | 3-Chlorophenyl |
| 5 | Methyl | Methyl | 2-Methoxyphenyl |
| 6 | Methyl | Methyl | Phenyl* |
| 7 | Ethyl | Ethyl | 2-Fluorophenyl |
| 8 | Hexamethylene | | Phenyl |
| 9 | (3-Methyl)pentamethylene | | Phenyl |
| 10 | Trifluoromethyl | H | Phenyl |

-continued

| Compound | Ra | Rb | Benzene Ring B |
|---|---|---|---|
| 11 | 2-Chlorophenyl | H | Phenyl |
| 12 | 3-Chlorophenyl | H | Phenyl |
| 13 | 4-Chlorophenyl | H | Phenyl |
| 14 | 3-Fluorophenyl | H | Phenyl |
| 15 | 4-Fluorophenyl | H | Phenyl |
| 16 | 2-Methylphenyl | H | Phenyl |
| 17 | 2-Ethylphenyl | H | Phenyl |
| 18 | 4-Methoxyphenyl | H | Phenyl |
| 19 | 3-Methylthiophenyl | H | Phenyl |
| 20 | Isopropyl | H | Phenyl |
| 21 | 3,4-Methylenedioxyphenyl | H | Phenyl |
| 22 | 3,4-(Methyleneoxymethylene)phenyl | H | Phenyl |
| 23 | Methyl | H | Phenyl |
| 24 | Methyl | Methyl | 2-Methylphenyl |
| 25 | Methyl | Methyl | 2-Hydroxyphenyl |

*methanesulphonamido derivative.

The antagonism of the effects of $TXA_2$ on the vasculature may be demonstrated in the following manner:

Male rats (Alderley Park strain) are anaesthetised with sodium pentabarbital and blood pressure is monitored at the carotid artery. The $TXA_2$ mimetic agent known as U46619 (e.g. R. L. Jones, et alia, in "Chemistry, Biochemistry and Pharmacological Activity of Prostanoids" eds. S. M. Roberts and F. Scheinmann, at p.211; Pergamon Press, 1979) is administered intravenously via the jugular vein and an $ED_{50}$ (dose necessary to produce 50% of the maximum hypertensive effect) is established (n=3). The $ED_{50}$ for U46619 is approximately 5 μg/kg. A test compound is then administered either intravenously via the jugular vein or orally via a cannula directly into the stomach and the animal challenged with an $ED_{50}$ dose of U46619, five minutes after dosing with test compound and then successively every ten minutes until the hypertensive effect of U46619 is no longer blocked.

By way of illustration only, in this test the laevorotatory form of 5(Z)-(2,2-diethyl-4-phenyl-1,3-dioxan-cis-5-yl)heptenoic acid showed significant reduction (>30%) of the hypertensive effects of the $TXA_2$ mimetic U46619 for a period of 120 minutes after oral administration at 50 mg./kg. However, in general preferred compounds of formula I show significant reduction of the hypertensive effect of U46619, for example for at least 60 minutes after intravenous administration at 10 mg./kg. or less, without any signs of overt toxicity at the active dose. Other illustrative compounds of the invention which may be mentioned as showing significant reduction of the hypertensive effects of U46619 for at least 60 minutes after oral administration in the above test are, for example, compounds 1, 2, 3, 5, 11, 13, 20, 21, 23 and 24 in the above list.

As stated previously, the compounds of formula I may be used in the therapy or prevention of diseases or adverse conditions in warm-blooded animals in which it is desirable to antagonise one or more of the actions of $TXA_2$. In general, a compound of formula I will be administered for this purpose by an oral, rectal, intravenous, subcutaneous, intramuscular or inhalation route, so that a dose in the range, for example 0.5–20 mg./kg. body weight, will be given up to four times per day, varying with the route of administration, the severity of the condition and the size and age of the patient under treatment.

The compounds of formula I will generally be used in the form of a pharmaceutical composition comprising a compound of formula I or, where appropriate, a salt thereof as defined hereinbefore, together with a pharmaceutically acceptable diluent or carrier. Such compositions are provided as a further feature of the invention and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection; in the form of aerosols or nebuliser solutions or suspensions for administration by inhalation; and in the form of powders together with pharmaceutically acceptable inert solid diluents such as lactose for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example, a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplants. When used for this purpose a compound of formula I or a physiologically acceptable salt thereof will generally be administered so that a steady state concentration in the range, for example, 0.5 to 50 mg. per liter is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°–26° C.;

(iii) column chromatography was performed on Merck Kieselgel 60 (Art, 7734) using approximately 50–70 g. of $SiO_2$ per g. of sample, and monitoring the process by thin layer chromatography on Merck 0.25 mm. Kieselgel 60F 254 plates (Art. 5715), flash chromatography was performed on Merck Kieselgel (Art 9385); these materials were obtained from E. Merck, Darmstadt, W. Germany;

(iv) yields are given for illustration only and are not necessarily the maximum attainable;

(v) NMR spectra were normally determined at 90 MHz in CDCl$_3$ using tetramethylsilane (TMS) as an internal standard, and expressed as chemical shifts (delta values) relative to TMS using the following abbreviations for designation of major peaks: s, singlet; m, multiplet; t, triplet; br, broad; d, doublet.

When a single chemical shift value is given for a multiplet (m) this corresponds to the centre point of the signals making up the multiplet;

(vi) all end-products were isolated as racemates, and (vii) those compounds of formula I wherein A is vinylene may contain 3–5% by weight of the E-stereoisomeric form.

EXAMPLE 1

(2,2-Dimethyl-4-phenyl-1,3-dioxan-cis-5-yl)acetaldehyde (2.0 g.) was added under argon with stirring and ice-cooling to a solution of the ylid prepared from (4-carboxybutyl)triphenylphosphonium bromide (11.5 g.) and dimsyl sodium (5.4 g.) in dry dimethyl sulphoxide (150 ml.) and the mixture was stirred overnight. Cautious addition of water (200 ml.) followed by extraction with ether (3×150 ml.) removed the bulk of neutral material; acidification of the aqueous layer to pH 5–6 with aqueous oxalic acid followed by extraction with ether, drying (Na$_2$SO$_4$) and evaporation, gave the crude product as a yellow oil. Column chromatography, eluting with toluene/ethyl acetate/acetic acid (80:20:2 v/v) gave 5(Z)-7-(2,2-dimethyl-4-phenyl-1,3-dioxan-cis-5-yl)heptenoic acid as an oil (1.8 g.) which solidified on standing to give material of m.p. 76°–78° C.; NMR: 1.55 (6H,s), 1.3–2.6 (9H,m), 3.7–4.3 (2H,m), 5.1–5.5 (3H,m), 7.3 (5H, br s) and 9.59 (1H,s) ppm.

The starting material was obtained as follows:

A solution of ethyl 2-allyl-3-oxo-3-phenyl propionate * (10 g.) in dry tetrahydrofuran (20 ml.) was added over 5 minutes to a suspension of lithium aluminium hydride (2 g.) in tetrahydrofuran (130 ml.) with stirring at −78° C. under argon. The mixture was allowed to warm to room temperature, stirred for 6 hours and was then treated with ethyl acetate (25 ml.) and saturated aqueous ammonium chloride solution (100 ml.). Filtration, extraction of the aqueous phase with ether (3×150 ml.), drying the ether layer (Na$_2$SO$_4$) and evaporation gave a pale brown oil (10 g.). Column chromatography, eluting with chloroform/ethyl acetate (9:1 v/v) gave 2-allyl-1-phenyl-1,3-propanediol as a colourless oil (5.4 g.); NMR: 1.6–2.2 (3H,m), 3.0 (1H,s), and 7.3 (5H,br s).
[* Obtained as an oil by an analogous procedure to that of C. S. Marvel and F. D. Hager, *Organic Syntheses*, Coll., Vol I, p. 248].

A solution of 2-allyl-1-phenyl-1,3-propanediol (5.4 g.) in 2,2-dimethoxypropane (250 ml.) was treated with p-toluenesulphonic acid (25 mg.) and allowed to stand overnight at room temperature. Addition of triethylamine (5 drops) followed by evaporation gave a brown oil which on flash column chromatography, (silica 30:1 per g. sample weight), eluting with toluene/hexane (1:1 v/v) gave (4,5-cis)-5-allyl-2,2-dimethyl-4-phenyl-1,3-dioxane as a colourless oil (2.1 g.) which solidified on standing to give material of m.p. 41°–43° C.; NMR: 1.55 (6H,s), 1.2–1.6 (3H,m), 3.8–4.2 (2H,m), 4.8–5.9 (3H,m), 5.2 (1H,d, J=2.7 Hz) and 7.3 (5H, br s) ppm. and (4,5-trans)-5-allyl-2,2-dimethyl-4-phenyl-1,3-dioxane as a colourless oil (1.8 g.) which solidified on standing to give material of m.p. 31°–34° C.; NMR: 1.4 (3H,s), 1.5 (3H,s), 1.3–2.2 (3H,m), 3.5–4.0 (2H,m), 4.5 (1H,d,J=10 Hz), 4.7–5.8 (3H,m) and 7.3 (5H,br s) ppm. Ozone was passed through a solution of (4,5-cis)-5-allyl-2,2-dimethyl-4-phenyl-1,3-dioxane (2.1 g.) in methylene chloride (200 ml.) at −78° C. until a permanent blue colour developed. The solution was flushed with argon until colourless. A solution of triphenylphosphine (2.1 g.) in dichloromethane (40 ml.) was added and the mixture was allowed to warm to room temperature. Evaporation followed by column chromatography, eluting with chloroform/ethyl acetate (19:1 v/v) gave (2,2-dimethyl-4-phenyl-1,3-dioxan-cis-5-yl)acetaldehyde as a white solid (2.0 g.), m.p. 67°–69° C.; NMR: 1.55 (6H,s), 2.0–3.1 (3H,m), 3.7–4.4 (2H,m), 5.2 (1H,d,J=2.0 Hz) and 7.3 (5H,br s) ppm.

EXAMPLE 2

Diazomethane was distilled into a solution of 5(Z)-7-(2,2-dimethyl-4-phenyl-1,3-dioxan-cis-5-yl)heptenoic acid (320 mg.) in dry ether (10 ml.) with ice-cooling until a yellow-green colour persisted in the mixture. A solution of acetic acid in ether (10% v/v) was added until effervescence ceased. The mixture was concentrated, diluted with tetrachloromethane (20 ml.), decolourised with activated charcoal at room temperature and evaporated to give methyl 5(Z)-7-(2,2-dimethyl-4-phenyl-1,3-dioxan-cis-5-yl)heptenoate as a colourless oil (300 mg.); NMR: 1.5 (6H,s), 1.4–2.4 (9H,m), 3.65 (3H,s), 3.7–4.3 (2H,m), 5.2 (3H,m) and 7.3 (5H,s) ppm; m/e 332 (M+).

EXAMPLE 3

In a similar manner to Example 1, except that (4-carboxypentyl)triphenylphosphonium bromide was used instead of (4-carboxybutyl)triphenylphosphonium bromide, there was obtained 6(Z)-8-(2,2-dimethyl-4-phenyl-1,3-dioxan-cis-5-yl)octenoic acid as a colourless oil (2.2 g.); NMR: 1.5 (6H,s), 1.2–3.5 (11H,m), 3.7–4.3 (2H,m) and 7.3 (5H,m) ppm; m/e 404[M+ +(CH$_3$)$_3$Si].

EXAMPLE 4

In a similar manner to Example 1, but starting from (2,2-diethyl-4-phenyl-1,3-dioxan-cis-5-yl)acetaldehyde, there was obtained 5(Z)-7-(2,2-diethyl-4-phenyl-1,3-dioxan-cis-5-yl)heptenoic acid as a colourless oil in 45% yield; NMR: 0.7–1.2 (6H,m), 1.3–2.6 (13H,m), 3.7–4.3 (2H,m), 5.1–5.5 (3H,m) and 7.3 (5H, br s) ppm; m/e: 347 (M+ +H) and 317 (M+ —C$_2$H$_5$).

The starting material was obtained as follows:

A solution of (4,5-cis)-5-allyl-2,2-dimethyl-4-phenyl-1,3-dioxane (20 g.) in tetrahydrofuran (400 ml.) was treated with a solution of hydrochloric acid (2M, 10 ml.) in water (100 ml.) and the resulting solution was heated under reflux for 3 hours. The mixture was evaporated. The brown oil obtained was dissolved in ethyl acetate (200 ml.). The solution was washed with water (3×100 ml.), dried (Na$_2$SO$_4$) and evaporated to give crude erythro-2-allyl-1-phenyl-1,3-propanediol (17 g.) as a colourless oil which was used without further purification.

A solution of crude erythro-2-allyl-1-phenyl-1,3-propanediol (17 g.) in toluene (200 ml.) containing 3-pentanone (10 g.) and p-toluenesulphonic acid (50 mg.) was heated under reflux for 4 hours using a Dean and Stark apparatus for removal of water. The reaction mixture was diluted with toluene (100 ml.), washed with aqueous sodium hydroxide (2M, 50 ml.) and then water (100 ml.), dried (Na$_2$SO$_4$) and evaporated to give a brown oil which on column chromatography, eluting with toluene, gave (4,5-cis)-5-allyl-2,2-diethyl-4-phenyl-1,3-dioxane (5.8 g.) as a colourless oil; NMR: 0.7–1.2 (6H,m), 1.4–2.6 (7H,m), 3.7–4.3 (2H,m), 4.7–5.9 (3H,m), 5.2 (1H,d, J=3 Hz) and 7.3 (5H,m) ppm.

Ozone was passed through a solution of (4,5-cis)-5-allyl-2,2-diethyl-4-phenyl-1,3-dioxane (5.8 g.) in dichloromethane (600 ml.) at −78° C. until a permanent blue colour developed. The solution was flushed with argon until colourless. A solution of triphenylphosphine (7.5 g.) in dichloromethane (150 ml.) was then added and the mixture was stirred overnight at −20° C. and for 3 hours at room temperature. The mixture was evaporated and the residue was purified by column chromatography, eluting with chloroform/ethyl acetate (19:1, v/v) to give (2,2-diethyl-4-phenyl-1,3-dioxan-cis-5-yl)acetaldehyde as a colourless oil (4.3 g.); NMR: 0.7–1.2 (6H,m), 1.6–3.0 (7H,m), 3.6–4.4 (2H,m), 5.2 (1H,d, J=2.4 Hz), 7.3 (5H, br s) and 9.5 (1H,s) ppm.

EXAMPLE 5

In a similar manner to Example 1, but starting from [2,2-dimethyl-4-(2-methylphenyl)-1,3-dioxan-cis-5-yl]acetaldehyde, there was obtained 5(Z)-7-[2,2-dimethyl-4-(2-methylphenyl)-1,3-dioxan-cis-5-yl]heptenoic acid as a white solid (0.69 g.); m.p. 72°–75° C.; NMR: 1.55 (6H,s), 2.3 (3H,s), 1.3–2.7 (9H,m), 3.7–4.3 (2H,m), 5.0–5.6 (3H,m) and 7.1–7.6 (4H,m) ppm; m/e: 333 [M+ +H].

The starting material was obtained as an oil using an analogous procedure to that described in Example 1; NMR: 1.5 (3H,s), 1.6 (3H,s), 1.8–2.9 (3H,m), 2.4 (3H,s), 3.6–4.2 (2H,m), 4.9 (1H,d, J=9 Hz), 7.1–7.6 (4H,m) and 9.45 (1H,s) ppm; starting from ethyl 2-allyl-3-(2-methylphenyl)-3-oxopropionate, itself obtained as an oil using a similar procedure to that of C. S. Marvel and F. D. Hager, *Organic Syntheses* Coll. Vol.I, p.248.

The following intermediates analogous to those in Example 1 were isolated:

(a) 2-allyl-1-(2-methylphenyl)-1,3-propanediol as a colourless oil; NMR: 1.6–2.6 (3H,m), 2.3 (3H,s), 3.7 (2H,d), 4.8–6.0 (4H,m) and 7.0–7.7 (4H,m) ppm;

(b) (4,5-cis)-5-allyl-2,2-dimethyl-4-(2-methylphenyl)-1,3-dioxane as an oil; NMR: 1.3–2.6 (3H,m), 1.55 (6H,s), 2.3 (3H,s), 3.7–4.3 (2H,m), 4.8–5.8 (3H,m), 5.3 (1H,d, J=2.7 Hz) and 7.0–7.7 (4H,m) ppm.

EXAMPLE 6

In a similar manner to Example 1, but starting from (4-phenyl-1,3-dioxan-cis-5-yl)acetaldehyde, there was obtained: 5(Z)-7-(4-phenyl-1,3-dioxan-cis-5-yl)heptenoic acid as a colourless oil in 61% yield, which solidified to give material of m.p. 42°–46° C.; NMR: 1.5–2.6 (9H,m), 3.7–4.3 (2H,m), 4.8–5.6 (5H,m) and 7.3 (5H,br s) ppm; m/e 290 [M+].

The starting material was obtained as follows:

A solution of crude erythro-2-allyl-3-phenyl-1,3-propanediol (50 g.) in toluene (100 ml.) containing dimethoxymethane (5 ml.) and p-toluenesulphonic acid (25 mg.) was heated under reflux for 2 hours. Further dimethoxymethane (2 ml.) was added and heating was continued for 1 hour. The reaction mixture was cooled and washed with water (2×50 ml.). The organic phase was dried (Na$_2$SO$_4$) and evaporated. The brown oil obtained was purified by column chromatography, eluting with toluene to give (4,5-cis)-5-allyl-4-phenyl-1,3-dioxane (A) (520 mg.) as a colourless oil; NMR 1.5–2.6 (3H,m), 3.7–4.3 (2H,m), 4.8–5.9 (5H,m), 5.3 (1H,d, J=6 Hz) and 7.3 (5H, br s) ppm.

A solution of A (500 mg.) in t-butyl alcohol (5 ml.) was added to a solution containing sodium periodate (1.2 g.), water (5 ml.), t-butyl alcohol (35 ml.) and osmium tetroxide (5 mg.). The mixture was stirred for 3 hours. Water (100 ml.) was added to dissolve the precipitate and the aqueous solution was extracted with toluene (3×50 ml.). The extracts were dried (Na$_2$SO$_4$), evaporated and gave, after column chromatography, eluting with chloroform/ethyl acetate (19:1 v/v), (4-phenyl-1,3-dioxan-cis-5-yl)acetaldehyde as a colourless oil (200 mg.); NMR: 2.1–3.2 (3H,m), 4.1 (2H,m), 4.9–5.4 (3H,m), 7.3 (5H, br s) and 9.6 (1H,br s) ppm.

EXAMPLE 7

A solution of 3-(2,2-dimethyl-4-phenyl-1,3-dioxan-cis-5-yl)propionaldehyde (500 mg.) in dry dimethyl sulphoxide (5 ml.) was added under argon with ice-cooling to a stirred solution of the ylid prepared from (4-carboxypropyl)triphenylphosphonium bromide (2.4 g.) and dimsyl sodium (1.2 g.) in dry dimethyl sulphoxide (20 ml.). The mixture was stirred for 18 hours. Water (50 ml.) was added and the aqueous mixture was extracted with ether (3×50 ml.) to remove the bulk of the neutral material. The aqueous layer was acidified to pH 5–6 (2M hydrochloric acid) and extracted with ether (4×50 ml.). The combined extracts were dried (Na$_2$SO$_4$) and evaporated. The residual yellow oil was purified by column chromatography eluting with toluene/ethyl acetate/acetic acid (80/20/2 v/v/v) to give 4(Z)-7-(2,2-dimethyl-4-phenyl-1,3-dioxan-cis-5-yl)-heptenoic acid as an oil (300 mg.); NMR: 1.5 (6H,s), 1.3–2.6 (9H,m), 3.7–4.3 (2H,m), 4.9–5.4 (3H,m) and 7.3 (5H,br s) ppm; m/e: 191, 107 and 91.

The starting material was obtained as follows:

A solution of borane in tetrahydrofuran (1M, 11 ml.) was added over 10 minutes to an ice-cooled, stirred solution of (4,5-cis)-5-allyl-2,2-dimethyl-4-phenyl-1,3-dioxane (2.32 g.) in dry tetrahydrofuran (50 ml.) under argon. Stirring was continued for 30 minutes and the mixture was treated sequentially with aqueous sodium hydroxide (1M, 20 ml.) and hydrogen peroxide (30% w/v; 5 ml.). After a further 30 minutes, saturated brine (100 ml.) was added and the mixture was extracted with ethyl acetate (3×70 ml.). The extracts were dried (Na$_2$SO$_4$) and evaporated to give 3-(2,2-dimethyl-4-phenyl-1,3-dioxan-cis-5-yl)-1-propanol (B) (2.6 g.) as a colourless oil which was used without further purification. A suspension of pyridinium chlorochromate (1.62 g.) in dichloromethane (25 ml.) was treated with a solution of B (1.25 g.) in dichloromethane (10 ml.). The mixture was stirred for 40 minutes. Ether (100 ml.) was then added and the solution was poured through a short column containing activated magnesium silicate (25 g., 60–100 Mesh). The column was thoroughly eluted with ether and the eluate was evaporated. The residual oil was purified by column chromatography, eluting with chloroform/ethyl acetate (9:1 v/v), to give 3-(2,2-dimethyl-4-phenyl-1,3-dioxan-cis- 5-yl)propionaldehyde as a colourless oil (550 mg.); NMR: 1.55 (6H,s), 1.2–2.3 (5H,m), 3.7–4.3 (2H,m), 5.2 (1H, br s), 7.3 (5H, br s) and 9.55 (1H,s) ppm.

EXAMPLE 8

A solution containing erythro-5(Z)-9-hydroxy-8-hydroxymethyl-9-phenylnonenoic acid (140 mg.), p-toluenesulphonic acid (5 mg.) and phenylacetaldehyde dimethyl acetal (125 μl.) in dry tetrahydrofuran (5 ml.) was heated at 60°–65° C. for 24 hours. The cooled reaction mixture was evaporated and the residue diluted with ether (10 ml.). The solution obtained was washed with water (5 ml.), saturated aqueous sodium bicarbonate (5 ml.), water (5 ml.) and saturated brine (5 ml.) then dried (MgSO$_4$) and evaporated to give a yellow oil, which was purified by column chromatography, eluting with dichloromethane/methanol (19:1 v/v), to give 5(Z)-7-(2-benzyl-4-phenyl-1,3-dioxan-cis-5-yl)heptenoic acid as a pale yellow oil (100 mg.); NMR: 1.3–2.6 (9H,m), 3.0 (2H,d), 3.7–4.3 (2H,m), 4.8–5.5 (4H,m) and 7.3 (5H,br s) ppm; microanalysis, found: C, 75.7; H, 7.6%; calculated: C, 75.79; H, 7.37%.

The starting material was obtained as follows:

A solution containing 5(Z)-7-(2,2-dimethyl-4-phenyl-1,3-dioxan-cis-5-yl)heptenoic acid (5.2 g.), water (20 ml.) and aqueous hydrochloric acid (2M, 3 ml.) in tetrahydrofuran (180 ml.) was heated at 60°–70° C. for 3 hours and then evaporated. The residue obtained was diluted with ethyl acetate (100 ml.), washed with water (3×100 ml.), dried (Na$_2$SO$_4$) and evaporated to give crude erythro-5(Z)-9-hydroxy-8-hydroxymethyl-9-phenyl-5-nonenoic acid as a colourless oil (4.5 g.) which was used without further purification.

EXAMPLE 9

Using a similar procedure to that in Example 8, but starting from cyclohexanone diethyl acetal, there was obtained 5(Z)-7-(4'-phenyl-[cyclohexanespiro-2'-1,3-dioxan]-cis-5'-yl)heptenoic acid as a colourless oil, which solidified on standing to give material of m.p 76°–79° C.; NMR: 1.3–2.7 (19H,m), 3.7–4.3 (2H,m), 5.2–5.6 (3H,m) and 7.3 (5H, br s) ppm; m/e: 358 (M+).

EXAMPLES 10–22

Using a similar procedure to that described in Example 1, but staring from the appropriate aldehyde of formula II (n=1) and the ylid from (4-carboxybutyl)triphenylphosphonium bromide, the following compounds of the formula Ib (Ra=Rb=methyl)

| Ex. | Ring B Subs. | m.p. (°C.) | NMR (Ring B-1H) ppm | Mass Spectrum m/e | Base/ Yield (%) |
|---|---|---|---|---|---|
| 10 | 2-Cl | 58–62 | 7.28 (3H,m) 7.75 (1H,m) | (M + H) 353 | D/63 |
| 11 | 2-F | 71–74 | 7.07 (3H,m) 7.5 (1H,m) | (M + H) 337 | D/35 |
| 12 | 2-CF$_3$ | oil | 7.55 (4H,m) | (M + H) 387 | D/33 |
| 13 | 2-OMe | 112–114 | 7.1 (4H,m) 3.7 (3H,s,OMe) | (M + H) 349 | T/59 |
| 14 | 2-Pr$^i$ | oil | 7.2 (3H,m) 7.3 (1H,m) 3.03 (1H,m) 1.21 (6H,d) | (M + H) 361 | D/32 |
| 15 | 2-Et | oil | 7.17 (3H,m) 7.46 (1H,m) 2.57 (2H,q) 1.16 (3H,t) | (M + H) 347 | T/81 |
| 16 | 2,6-F$_2$ | oil | 6.86 (3H,m) 7.19 (1H,m) | (M + H) 355 | T/44 |
| 17 | 3-F | 50–53 | 6.8–7.5 (4H,m) | (M—Me) 321.150 | D/27 |
| 18 | 4-Me | 94–99 | 7.1–7.28 (4H,m) 2.3 (3H,s, CH$_3$) | (M + H) 333 | T/80 |
| 19 | 3-CF$_3$ | 55–58 | 7.4–7.58 (4H,m) | (M—Me) 386.1698 | T/93 |
| 20 | 3-Cl | oil | 7.0–7.3 (4H,m) | (M—Me) 337.120 | T/60 |
| 21 | 4-NO$_2$ | oil | 7.4–8.4 (4H,m) | (M) | |
| 22 | 4-F | 74–77 | 6.9–7.4 (4H,m) | 363.1671 (M + H) 337 | B/69 T/75 |

Notes:
$^1$NMR: determined at 90 MHz in CDCl$_3$; all the spectra contained the following additional signals: 1.55(6H,s,CH$_3$), 1.3–2.6(9H,m; CH$_2$,CH), 3.7–4.3 (2H,m,OCH$_2$) and 5.1–5.5 (3H,m; CH=CH, OCHPh).
(ii) Bases used for generation of ylid:
D = dimsyl sodium + dimethyl sulphoxide;
T = potassium t-butoxide + tetrahydrofuran;
B = butyl lithium + tetrahydrofuran.
The solvent used for the generation of the ylid was used for the reaction between the ylid and the aldehyde of formula II.
(iii) For Ex. 21, the ylid was added to a solution of the aldehyde in tetrahydrofuran at −70° C.

The necessary starting aldehydes of formula II (Ra=Rb=CH$_3$, n=1) were obtained in yields of 56–95% from the corresponding derivatives of formula VII (Ra=Rb=methyl) in an analogous manner to that described in Example 1 starting from the appropriate ethyl 2-allyl-3-(substituted phenyl)-3-oxopropionate of formula V (R=ethyl). The aldehydes had the following properties:

| No. | Ring B Subs | NMR (Ring B-$^1$H) | IR (—CHO) cm$^{-1}$ | Physical Form |
|---|---|---|---|---|
| 10a | 2-Cl | 7.25 (3H,m) 7.55 (1H,m) | 1720 | oil |
| 11a | 2-F | ** | 1720 | oil |
| 12a | 2-CF$_3$ | ** | 1720 | oil |
| 13a | 2-OMe | ** | 1720 | oil |
| 14a | 2-Pr$^i$ | ** | 1720 | oil |
| 15a | 2-Et | ** | 1720 | oil |
| 16a | 2,6-F$_2$ | 7.12 (3H,m) | 1720 | solid m.p. 46–47° C. |
| 17a | 3-F | ** | 1720 | oil |
| 18a | 4-Me | ** | 1720 | oil |
| 19a | 3-CF$_3$ | ** | 1720 | oil |
| 20a | 3-Cl | ** | 1720 | oil |
| 21a | 4-NO$_2$ | 7.4–8.4 (4H,m) | 1715 | oil |
| 22a | 4-F | ** | 1720 | oil |

Notes:
IR: Infra-red spectra were generally determined as liquid films on rock-salt plates.
NMR: All the spectra contained the following additional signals: 1.55 (6H,s,CH$_3$), 2.0–3.1 (3H,m,CH—CH$_{2CHO}$), 3.7 (2H, m, OCH$_2$) and 5.2 (1H, d, J = 2Hz,OCHPh).
**NMR spectrum not determined; material essentially pure by thin layer chromatography (TLC) (SiO$_2$:1:9 v/v ethyl acetate/chloroform).

The following intermediate (4,5-cis)-5-ally-2,2-dimethyl-4-phenyl-1,3-dioxane of of formula VII (Ra=Rb=Methyl) were isolated (any isomeric (4,5-trans)-5-allyl-2,2-dimethyl-4-phenyl-1,3-dioxane being removed by chromatography):

| No. | Ring B Subs | NMR (Ring B-$^1$H) | Yield (%) | Physical Form |
|---|---|---|---|---|
| 10b | 2-Cl | 7.27 (3H,m) 7.61 (1H,m) | 38 | oil |
| 11b | 2-F | 7.07 (3H,m) 7.49 (1H,m) | 24 | oil |
| 12b | 2-CF$_3$ | 7.52 (4H,m) | 10 | oil |
| 13b | 2-OMe | 7.11 (4H,m) 3.82 (3H,s,OMe) | 56 | Solid m.p. 77–79° C. |
| 14b | 2-Pr$^i$ | | 21 | oil |
| 15b | 2-Et | 7.17 (3H,m) 7.42 (1H,m) 1.21 (3H,m,Me) | 42 | oil |
| 16b | 2,6-F$_2$ | 6.95 (2H,m) 7.31 (1H,m) | 80 | oil |

-continued

| No. | Ring B Subs | NMR (Ring B-¹H) | Yield (%) | Physical Form |
|---|---|---|---|---|
| 17b | 3-F | 6.8–7.45 (4H,m) | 28 | oil |
| 18b | 4-Me | 7.0–7.25 (4H,m) 2.3 (3H,s,CH₃) | 21 | oil |
| 19b | 3-CF₃ | 7.4–7.65 (4H,m) | 30 | oil |
| 20b | 3-Cl | 7.1–7.35 (4H,m) | 26 | oil |
| 21b | 4-NO₂ | 7.4–8.4 (4H,m) | 33 | oil |
| 22b | 4-F | 6.9–7.4 (4H,m) | 39 | oil |

Notes:
NMR: the following NMR signals were common to all the compounds: 1.55 (6H,s), 1.2–1.6 (3H,m), 3.8–4.2 (2H,m), 4.8–5.9 (3H,m) and 5.2 (1H,d, J = 2.7 Hz.).

Yields: yields quoted are from the 2-allyl-3-(substituted phenyl)-3-oxo-propionate of formula V (Ra=Rb=methyl, R=ethyl). That quoted for No. 16b is from essentially pure erythro-2-allyl-1-(2,6-difluorophenyl)-1,3-propanediol and that quoted for No. 13b is from 4:1 erythro- to threo-2-allyl-1-(2-methoxyphenyl)-1,3-propanediol.

The 5-allyl-1,3-dioxane derivatives of formula VII (Ra=Rb=methyl) were themselves obtained by cyclisation of the erythro-form of the appropriate 2-allyl-1-(substituted phenyl)-1,3-propanediol of formula VIa (Ra=Rb=methyl) in the presence of 2,2-dimethoxypropane by analogy with the procedure in Example 1. The required erythro-diols of formula VIa were generally obtained, together with the corresponding threo-diols of formula VIb, as oils by lithium aluminium hydride or lithium borohydride reduction of the ethyl 2-allyl-3-(substituted phenyl)-3-oxopropionate of formula V and were used without special purification or characterisation.

Alternatively the erythro- diol of the formula VIa may be obtained essentially free of the threo-isomer VIb by a two stage reduction procedure using first zinc borohydride followed by lithium aluminium hydride. The latter procedure is illustrated by the production of erythro-2-allyl-1-(2,6-difluorophenyl)-1,3-propanediol:

(a) A solution of anhydrous zinc chloride (1.7 g.) in anhydrous ether (20 ml.) was added to a stirred suspension of sodium borohydride (1.1 g.) in anhydrous ether (40 ml.) and the mixture stirred for 18 hours. Solid material was removed by filtration. A solution of ethyl 2-allyl-3-(2,6-difluorophenyl)-3-oxopropionate (1.4 g.) in anhydrous ether (10 ml.) was then added over 5 minutes to the filtrate which had been cooled to 0° C. The subsequent mixture was stirred at 0° C. for 45 minutes. 2M Hydrochloric acid was then added until gas evolution ceased. The organic phase was separated, washed with saturated brine, dried (MgSO₄) and evaporated. The oil (1.3 g.) obtained was purified by flash column chromatography on silica (40 g.) using 15% v/v ethyl acetate in petroleum ether (b.p. 60°–80° C.) as eluent to give ethyl erythro-2-allyl-3-(2,6-difluorophenyl)-3-hydroxypropionate (A) (400 mg.) as an oil; NMR: 1.02 (3H,t), 2.58 (3H,m), 3.12 (1H,m), 3.90 (2H,q), 5.13 (3H,m), 5.83 (1H,m), 6.83 (2H,m) and 7 24 (1H,m) ppm.

(b) A solution of the ester (A) (340 mg.) in anhydrous ether (10 ml.) was added under nitrogen over 3 minutes to a stirred suspension of lithium aluminium hydride (120 mg.) in anhydrous ether (30 ml.) at 0° C. The mixture was heated under reflux for 30 minutes and cooled by ice-water. Ethyl acetate (2 ml.) in anhydrous ether (10 ml.) was then added, followed by saturated ammonium chloride solution (25 ml.). The mixture obtained was separated by filtration. The organic phase was washed with saturated brine, dried (MgSO₄) and evaporated to give erythro-2-allyl-1-(2,6-difluorophenyl)-1,3-propanediol as an oil (252 mg.); NMR 2.30 (5H,m), 3.60 (2H,d), 5.18 (3H,m), 5.9 (1H,m), 6.95 (2H,m) and 7.30 (1H,m) ppm.

The lithium borohydride procedure is illustrated by the production of 2-allyl-1-(2-ethylphenyl)-1,3-propanediol:

A solution of 2-allyl-3-(2-ethylphenyl)-3-oxopropionate (7.3 g.) in dry tetrahydrofuran (THF) (40 ml.) was added during 10 minutes to a stirred suspension of lithium borohydride (1.32 g.) in dry THF (40 ml.) at 0° C. under a nitrogen atmosphere. The mixture was then stirred at room temperature for 18 hours, cooled to 0°–5° C. and water (40 ml.) added. The aqueous mixture was acidified to pH 2 (concentrated hydrochloric acid) and extracted with ethyl acetate (3×120 ml.). The combined extracts were washed with saturated brine, dried (MgSO₄) and evaporated. The residual oil (6.1 g.) was purified by chromatography on silica (180 g.) using 3:7 v/v ethyl acetate/petroleum ether (b.p.60°–80° C.) to give 2-allyl-1-(2-ethylphenyl)propane-1,3-diol (containing approximately 4:1 erythro- to threo-forms) as an oil (4.0 g.); NMR: 1.19 (3H,m), 2.04 (5H,m), 2.59 (2H,m), 3.76 (2H,m), 5.02 (3H,m), 5.67 (1H,m), 7.17 (3H,m), and 7.47 (1H,m)ppm.

The starting ethyl 2-allyl-3-(substituted phenyl)-3-oxopropionates of formula V (R=ethyl) may be obtained as oils by allylation of the appropriate 3-(substituted phenyl)-3-oxopropionate using the general procedure of Marvel and Hager. Examples of esters of formula V obtained in this way are those wherein benzene ring B is 2-chloro-, 3-chloro, 3-fluoro-, 2-methoxy-, 2-isopropyl-, 2-trifluoromethyl, 3-trifluoromethyl- and 4-methyl-phenyl. The necessary starting 3-oxopropionates were made using one of the following well known, standard procedures:

(a) reaction of the appropriate substituted benzoyl chloride with t-butyl ethyl malonate and magnesium ethoxide to give the corresponding t-butyl ethyl 2-(substituted benzoyl)malonate which is then thermolysed at 100° C. in vacuo in the presence of p-toluenesulphonic acid (e.g. those 3-oxopropionates wherein benzene ring B is 2-chloro-, 2-methoxy-, 2-isopropyl-and 2-trifluoromethyl-phenyl); or (b) reaction of the appropriate substituted benzoyl chloride with the dilithium salt of monoethyl malonate (obtained from two molecular equivalents of butyl lithium in hexane at −70° C.) at −65° C., followed by acidification with concomitant decarboxylation at room temperature (e.g. those 3-oxopropionates wherein benzene ring B is 3-fluoro-, 3-chloro-, 3-trifluoromethyl-and 4-methyl-phenyl).

Alternatively, the starting 2-allyl-3-(substituted phenyl)-3-oxopropionates of formula V (R=ethyl) may be obtained from t-butyl ethyl malonate as illustrated below:

(a) Potassium carbonate (28.0 g.) was added to a stirred solution of t-butyl ethyl malonate (37.6 g.) in dry N,N-dimethylformamide (DMF) (100 ml.). After 1 hour allyl bromide (34 ml.) was added. The mixture was heated at 70° C. for 66 hours, cooled to room temperature and diluted with water (900 ml.). The mixture obtained was extracted with ethyl acetate (3×200 ml.). The extracts were dried (MgSO₄) and evaporated. The oil obtained was purified by flash column chromatography eluting with 1:15 v/v ethyl acetate/petroleum ether (b.p. 60°–80° C.) to give t-butyl ethyl 2-allylmalonate as a colourless oil (15.6 g.), b.p. 70°–72° C. at 0.2 mmHg; NMR: 1.21 (3H,t), 1.42 (9H,s), 2.66 (2H,m), 3.28 (1H,m), 4.16 (2H,q), 5.06 (2H,m) and 5.76 (1H,m) ppm.

(b) Sodium hydride (2.8 g., 50% w/w dispersion in mineral oil) was added over 15 minutes to an ice cooled solution of t-butyl ethyl 2-allylmalonate (13.4 g.) in dry DMF (120 ml.) under nitrogen. The mixture was stirred at room temperature for 45 minutes and cooled to 0° C. 2-Ethylbenzoyl chloride (10.1 g.) was added over 2 minutes and the mixture stirred at room temperature for 18 hours. The DMF was evaporated and the residue shaken with water (100 ml.) and ethyl acetate (200 ml.). The ethyl acetate phase was separated, washed with saturated brine, dried (MgSO$_4$) and evaporated. The oil obtained (21.8 g.) was purified by flash column chromatography on silica (650 g.) using toluene as eluant to give t-butyl ethyl 2-allyl-2-(2-ethylbenzoyl)malonate (14.3 g.) as an oil; NMR: 1.25 (15H,m), 2.7 (2H,q), 2.9 (2H,d), 4.12 (2H,q), 5.31 (2H,m), 6.05 (1H,m) and 7.35 (4H,m) ppm.

(c) A mixture of t-butyl ethyl 2-allyl-2-(2-ethylbenzoyl)malonate (14.3 g.), acetic anhydride (4 ml.) and p-toluenesulphonic acid (100 mg.) in acetic acid (200 ml.) was heated at 140° C. under nitrogen for 75 minutes and then evaporated. The residue was shaken with a mixture of saturated sodium bicarbonate solution (100 ml.) and ethyl acetate (100 ml.). The organic phase was dried (MgSO$_4$) and evaporated. The oil obtained (9.3 g.) was purified by flash column chromatography (280 g.) using toluene as eluant to give ethyl 2-allyl-3-(2-ethylphenyl)-3-oxopropionate (7.4 g.) as a pale yellow oil; NMR: 1.19 (6H,m), (2.74 (4H,m), 4.15 (3H,m), 5.05(2H,m), 5.79 (1H,m), 7.30 (3H,m) and 7.61 (1H,m)ppm.

An analogous procedure to (a)–(c) above was used in addition for the preparation of:

(i) ethyl 2-allyl-3-(2,6-difluorophenyl)-3-oxopropionate, obtained as an oil; NMR: 1.2 (3H,t), 2.70 (2H,m), 4.17 (3H,m), 4.92 (2H,m), 5.73 (1H,m), 6.95 (2H,m) and 7.26 (1H,m) ppm; and (ii) ethyl 2-allyl-3-(2-fluorophenyl)-3-oxopropionate, obtained as an oil; NMR: 1.23 (3H,t), 2.67 (2H,m), 4.20 (3H,m), 5.04 (2H,m), 5.83 (1H,m), 7.09 (2H,m), 7.37 (1H,m) and 7.73 (1H,m)ppm.

Characteristic NMR data for other representative 2-allyl-3-oxopropionates of formula V (R=ethyl) obtained as oils by direct sodium ethoxide allylation of the corresponding ethyl 3-(substituted phenyl)-3-oxopropionate are as follows:

(i) ethyl 2-allyl-3-(2-trifluoromethylphenyl)-3-oxopropionate; NMR: 1.21 (3H,m), 2.75 (2H,m), 4.14 (3H,m), 5.04 (2H,m), 5.90 (1H,m) and 7.59 (4H,m) ppm;

(ii) ethyl 2-allyl-3-(2-chlorophenyl)-3-oxopropionate; NMR: 1.20 (3H,m), 2.71 (2H,m), 4.18 (3H,m), 4.93 (2H,m), 5.73 (1H,m) and 7.34 (4H,m) ppm; and (iii) ethyl 2-allyl-3-(2-methoxyphenyl)-3-oxopropionate; NMR: 1.17 (3H,m), 2.69 (2H,m), 4.10 (6H,m), 5.00 (2H,m), 5.81 (1H,m), 6.95 (2H,m), 7.38 (1H,m) and 7.51 (1H,m) ppm.

EXAMPLES 23–24

Using a similar procedure to that described in Example 1 the following acids of formula I were obtained:

(Example 23): 5(Z)-7-([2,4,5-cis]-2-methyl-4-phenyl-1,3-dioxan-5-yl)heptenoic acid, as a solid in 55% yield, m.p. 31°–32° C.; NMR: 1.0–2.4 (12H,m), 3.7–4.3 (2H,m), 4.7–5.0 (2H,m), 5.1–5.5 (2H,m) and 7.1–7.5 (5H,m) ppm; starting from ([2,4,5-cis]-2-methyl-4-phenyl-1,3-dioxan-5-yl)acetaldehyde and using potassium t-butoxide and tetrahydrofuran instead of dimsyl sodium and dimethyl sulphoxide;

(Example 24) 5(Z)-7-(2,2-dipropyl-4-phenyl-1,3-dioxan-cis-5-yl)heptenoic acid as an oil in 60% yield; NMR: 0.8–2.8 (23H,m), 3.6–4.3 (2H,m), 5.0–5.6 (3H,m), 7.1–7.6 (5H,m) and 9.3 (1H,br s) ppm, starting from (2,2-dipropyl-4-phenyl-1,3-dioxan-cis-5-yl)acetaldehyde.

The starting acetaldehyde for 23 was obtained as an oil [NMR: 1.45 (3H,d, J=5.0 Hz), 2.1–3.1 (3H,m). 4.05 (2H,s), 4.7–5.1 (2H,m), 7.1–7.5 (5H,m) and 9.55 (1H,s)ppm] in 89% yield by oxidation of (2,4,5-cis-5-allyl-2-methyl-4-phenyl-1,3-dioxane, itself obtained as an oil [NMR: 1.45 (3H,d, J=5.0 Hz), 1.5–2.6 (3H,m), 3.7–4.3 (2H,m), 4.8–5.1 (4H,m), 5.3–5.8 (1H,m) and 7.1–7.5 (5H,m)ppm] in 79% yield by cyclisation of the erythroform of 2-allyl-1-phenyl-1,3-propanediol with acetaldehyde, using analogous procedures to those described for Example 1.

The starting acetaldehyde for 24 was obtained as an oil in 95% yield by oxidaton of (4,5-cis)-5-allyl-2,2-dipropyl-4-phenyl-1,3-dioxane using a similar procedure to that described in Example 4. The latter dioxane was itself obtained as an oil; NMR: 0.7–2.7 (17H,m), 3.7–4.2 (2H,m), 4.7–5.8 (4H,m) and 7.0–7.4 (5H,m)ppm, in 42% yield by reaction of erythro-2-allyl-1-phenyl-1,3-propanediol with 4-heptanone using a similar procedure to that described for the analogous compound in Example 4.

EXAMPLES 25–29

A mixture of cyclopentanone (0.165 ml.), erythro-5(Z)-9-hydroxy-8-hydroxymethyl-9-phenylnonenoic acid (0.52 g.), triethyl orthoformate (0.4 ml.) and p-toluenesulphonic acid (5 mg.) was stirred for 3 hours. Ether (25 ml.) was then added and the solution was extracted with a solution of potassium hydroxide (0.21 g.) in water (10 ml.). The basic extract was washed with ether (10 ml.) and then acidified to pH 4 (2M hydrochloric acid). The resultant emulsion was extracted with ether (2×30 ml.). The combined extracts were washed with water (3×20 ml.) and saturated brine (20 ml.), then dried (MgSO$_4$) and evaporated. The yellow oil obtained was purified by flash column chromatography, using 80:20:2 v/v toluene/ethyl acetate/acetic acid to give 5(Z)-7-(4'-phenyl-[cyclopentanespiro-2'-1,3-dioxan]-cis-5-yl)heptenoic acid (Example 25) as a colourless oil (400 mg.); NMR: 1.4–2.5 (17H,m), 3.7–4.2 (2H,m), 5.1 (1H,d, J=2Hz), 5.2–5.5 (2H,m) and 7.1–7.5 (5H,m); m/e: 344 (M$^+$)

Using a similar procedure, but starting from the appropriate ketone, the following acids of formula Ib wherein benzene ring B is unsubstituted were obtained:

(Example 26): Ra+Rb=trimethylene; as an oil in 37% yield; NMR: 1.3–2.7 (15H,m), 3.7–4.1 (2H,m), 5.0 (1H,d,J=2Hz), 5.1–5.5 (2H,m), 7.1–7.4 (5H,m) and 9.0 (1H,br s)ppm; m/e: 330 M$^+$.

(Example 27): Ra+Rb=hexamethylene; as an oil in 42% yield; NMR: 1.2–2.6 (21H,m), 3.6–4.3 (2H,m), 5.1–5.5 (3H,m) and 7.1–7.5 (5H,m)ppm; m/e:372 M$^+$.

(Example 28): Ra=Rb=butyl; as an oil in 10% yield; NMR: 0.7–2.6 (27H,m), 3.7–4.2 (2H,m), 5.1–5.4 (3H,m) and 7.1–7.4 (5H,m) ppm.

(Example 29): Ra=phenyl Rb=methyl; as an oil in 40% yield; NMR: 1.65 (3H,s), 7.0–7.6(10H,m) and 7.7–8.7(1H,br s) ppm;m/e:380 (M$^+$).

EXAMPLES 30-32

Using a similar procedure to that described in Example 8 but replacing phenylacetaldehyde dimethyl acetal by:

(a) 1,1-dimethoxyheptane, there was obtained 5(Z)-7-([2,4,5-cis]-2-hexyl-4-phenyl-1,3-dioxan-5-yl)heptenoic acid (Example 30) as a solid, m.p. 60°-62° C. in 74% yield; NMR: 0.9 (3H,t), 1.1-2.6 (17H,m), 3.7-4.2 (2H,m), 2.7 (1H,t,J=4.0 Hz), 4.9 (1H,d,J=3.0Hz), 5.1-5.5 (2H,m) and 7.1-7.4 (5H,m)ppm; and (b) 1,1-diethoxypropane, there was obtained 5(Z)-7-([2,4,5-cis]-2-ethyl-4-phenyl-1,3-dioxan-5-yl)heptenoic acid (Example 31) as an oil in 63% yield; NMR: 1.0 (3H,m), 1.3-2.6 (11H,m), 3.7-4.3 (2H,m), 4.7 (1H,t,J=5.0 Hz), 4.9(1H,d, J=3.0Hz), 5.1-5.5 (2H,m), 7.1-7.4(5H,m) and 8.2 (1H,br s)ppm.

Similarly, by using the procedure of Example 8 with erythro-5(Z)-9-hydroxy-8-hydroxymethyl-9-(2-methylphenyl)nonenoic acid (A) and 3,3-dimethoxypentane, there was obtained 5(Z)-7-(2,2-diethyl-4-(2-methylphenyl)-1,3-dioxan-cis-5-yl)heptenoic acid (Example 32) as an oil in 65% yield; NMR: 0.7-1.3 (6H,m), 1.4-2.6 (13H,m), 2.13 (3H,s), 3.6-4.2 (2H,m), 4.9-5.4 (3H,m) and 7.0-7.6 (4H,m).

The necessary starting acid (A) was obtained as an oil in a similar manner to the 9-phenyl analogue described for Example 8, but starting from 5(Z)-7-[2,2-dimethyl-4-(2-methylphenyl)-1,3-dioxan-cis-5-yl]heptenoic acid; NMR: 1.1-2.5 (9H,m), 2.3(3H,s), 3.8 (2H,d, J=5.0Hz), 4.6-5.6 (3H,m) and 7.0-7.7 (4H,m)ppm.

EXAMPLE 33

5(Z)-7-(2,2-Dimethyl-4-phenyl-1,3-dioxan-cis-5-yl)heptenoic acid (191 mg, 0.6 mM) was dissolved in dry toluene (10 ml.), and freshly-distilled benzaldehyde (212 mg., 1.2 mM) and p-toluenesulphonic acid (3 mg.) were added. The mixture was heated at 100° C., with stirring, while being protected from the atmosphere (drying tube), for 1-2 hours until thin layer chromatography (TLC) indicated completion of the reaction. The cooled reaction mixture was purified by flash column chromatography on silica (20 g.) eluting with 5% v/v methanol in methylene chloride. There was thus obtained 5(Z)-7-([2,4,5-cis]-2,4-diphenyl-1,3-dioxan-5-yl)heptenoic acid as a viscous oil (254 mg.); NMR: 1.4-2.8 (9H,m), 4.1-4.3 (2H,m), 5.1-5.5 (3H,m), 5.75 (1H,s), 7.2-7.7 (10H,m)ppm; m/e: 366 (M+), 348 (M-H₂O), 279 [M-(CH₂)₃.CO₂H], 260 (M-PhCHO).

EXAMPLES 34-64

Using a similar procedure to that described in Example 33 but replacing benzaldehyde by the appropriate substituted aldehyde of the formula Ra. CHO, the following acids of formula Ib (benzene ring B is unsubstituted, Rb=H) were obtained in yields of 37-92% using either 10% v/v methanol in methylene chloride, 40% v/v acetone in methylene chloride, or 40:10:1 by (volume) toluene/ethyl acetate/acetic acid as the eluant for the flash chromatography.

| Ex. | Ra | Form | $^1$H NMR (ppm) | Mass Spectrum (m/e M+) |
|---|---|---|---|---|
| 34 | 4Cl—Ph | oil | 7.2-7.7 (9H,m) 5.70 (1H,s) | 400,402 (3:1) |
| 35 | 4F—Ph | oil | 6.95-7.65 (9H,m) 5.70 (1H,s) | 384 |
| 36 | 2Cl—Ph | oil | 7.8-8.0 (1H,m) 7.25-7.6 (8H,m) 6.17 (1H,s) | 400,402 (3:1) |
| 37 | 3Cl—Ph (iii) | oil | 7.0-7.6 (9H,m) 5.7 (1H,s) | 400,402 (3:1) |
| 38 | 3Cl—Ph (iv) | oil | 7.0-7.6 (9H,m) 5.7 (1H,s) | 400,402 (3:1) |
| 39 | 3Cl—Ph (v) | oil | 7.0-7.6 (9H,m) 5.7 (1H,s) | 400-402 (3:1) |
| 40 | 2Me—Ph | oil | 7.7 (1H,dd;J10,3) 7.0-7.5 (8H,m) 5.85 (1H,s) 2.5 (3H,s) | 380 |
| 41 | 4Me—Ph | solid m.p. 93-95 °C. | 7.0-7.5 (9H,m) 5.65 (1H,s) 2.35 (3H,s) | 380 |
| 42 | 4NO₂—Ph | oil | 8.25 (2H,d;J8) 7.7 (2H,d;J8) 7.25 (5H,s) 5.75 (1H,s) | 429* |
| 43 | 4MeO—Ph | oil | 7.6-8.2 (1H,CO₂H) 7.5 (2H,d; J8.5) 7.35 (5H,s) 6.9 (2H,d; J8.5) 5.6 (1H,s) 3.8 (3H,s) | 396 |
| 44 | 3Br—Ph | oil | 7.15-8.2 (10H,m; aromatic + CO₂H) 5.65 (1H,s) | 462,464* (1:1) |
| 45 | 1-naphth | oil | 8.25 (1H,m) 8.0-7.7 (3H,m) 7.2-7.7 (9H,m; aromatic + CO₂H) | 416 |
| 46 | 2-naphth | solid m.p. 118-119° C. | 7.0-8.0 (13H,m; aromatic + CO₂H) 5.85 (1H,s) | 416 |
| 47 | 3Me—Ph | oil | 7.1-7.5 (10H,m; aromatic + CO₂H) 5.85 (1H,s) | 380 |
| 48 | 3,4Cl₂—Ph | oil | 7.1-8.5 (9H,m; aromatic + CO₂H) 5.65 (1H,s) | 452,454 456* |
| 49 | 4CF₃—Ph | oil | 7.75 (4H,s) 7.3 (5H,s) 5.8 (1H,s) | 434 |
| 50 | 3CF₃—Ph | oil | 7.0-8.8 (10H,m; aromatic + CO₂H) 5.75 (1H,s) | 452* |
| 51 | 3MeO—Ph | oil | 9.0-10.0 (1H; br CO₂H) 7.05-7.5 (8H,m) 6.85 (1H dd;J8,2) 5.7 (1H,s) 3.8 (3H,s) | 3.96 |
| 52 | 2F—Ph | oil | 8.0-9.4 (1H, br CO₂H) 7.75 (1H,m) 6.95-7.5 (8H,m) 6.05 (1H,s) | 402* |
| 53 | 2MeO—Ph | oil | 7.8 (1H,dd;J8,2) 7.2-7.5 (6H,m) 7.05 (1H,dt; J 1.5,8) 6.9 (1H,dd; J 1.5,8) 6.07 (1H,s) 3.85 (3H,s) | 396 |
| 54 | 4Br—Ph | oil | 7.5 (4H,m) 7.2 (5H,m) 5.7 (1H,s) | 462,464* |
| 55 | 4CN—Ph | oil | 8.0-9.2 (1H; br CO₂H) 7.7 (4H,m) 7.3 (5H,m) 5.75 (1H,s) | 409* |
| 56 | 3F—Ph | oil | 8.0-9.0 (1H, br CO₂H) | 384 |

-continued

| Ex. | Ra. | Form | $^1$H NMR (ppm) | Mass Spectrum (m/e M$^+$) |
|---|---|---|---|---|
| 57 | 2CF$_3$—Ph | oil | 6.8–7.4 (9H,m)<br>5.7 (1H,s)<br>7.3–8.7 (1H; br CO$_2$H)<br>8.1 (1H;d,J8)<br>7.2–7.8 (8H,m)<br>6.05 (1H,s) | 452* |
| 58 | 4MeS—Ph | oil | 8.3–9.2 (1H, br CO$_2$H)<br>7.5 (d, J8)<br>7.35 (s) } –9H<br>7.25 (d,J8)<br>5.7 (1H,s)<br>2.5 (3H,s) | 412 |
| 59 | 3HO—Ph | oil | 6.65–7.5 (9H,m)<br>6.0–6.65 (2H,br s) | 382 |
| 60 | 4AcNH—Ph | solid<br>m.p.<br>157–<br>159° C. | 8.9 (1H,br NH)<br>7.4–7.7 (4H,m)<br>7.1–7.4 (5H,m)<br>5.65 (1H,s)<br>2.1 (3H,s) | 441* |
| 61 | F$_5$—Ph | oil | 10.2–10.6 (1H, br CO$_2$H)<br>7.1–7.6 (5H,m)<br>6.1 (1H,s) | 456 |
| 62 | 3,4-OCH$_2$O—Ph | oil | 7.2–7.4 (5H,m)<br>7.1 (1H,br s)<br>7.05 (1H,dd;J8,2)<br>6.8 (1H,dd;J8,2)<br>5.95 (2H,s)<br>5.65 (1H,s) | 410 |
| 63 | 2,4—Me$_2$Ph | oil | 7.55 (1H,d,J8)<br>7.2–7.4 (5H,m)<br>7.05 (1H,dd,J8,2)<br>7.0 (1H,br s)<br>5.8 (1H,s)<br>2.4 (3H,s)<br>2.3 (3H,s) | 394 |
| 64 | 3,4-(CH$_2$—OCH$_2$)—Ph | oil | 7.1–7.6 (8H,m)<br>5.75 (1H,s)<br>5.2 (4H,s) | 408 |

Notes:
(i) NMR: all proton NMR were determined in CDCl$_3$ at 90 MHz except Ex. 60 which was determined in d$_6$-acetone; signals are given in the Table for ring B protons and the fragment Ra.CH, but the spectra additionally contain signals at 1.4–2.8 (9H,m), 4.1–4.3 (2H,m) and 5.1–5.5 (3H,m)ppm; coupling constants (J) are given in Hz;
(ii) MS: all mass spectra contained additional characteristic signals corresponding to m/e = M—Ra.CHO; those marked with an asterisk (*) were determined by chemical ionisation using ammonia and corresponding to m/e = M + NH$_4$ rather than m/e = M; relative strengths of isotopic values are given in parentheses;
(iv) dextrorotatory (+) enantiomer; $[\alpha]_D^{20} = 88°$ (c. 2.05, MeOH);
(v) laevorotatory (−) enantiomer; $[\alpha]_D^{20} = -92°$ (c. 1.52, MeOH);

The aldehyde starting material for Example 64 was obtained as follows:

To a solution of 1,3-dihydro(5-benzo[c]furyl)methanol (1.265 g.) in dry methylene chloride (10 ml.) was added pyridinium dichromate (3.23 g.) in one portion. The dark mixture was stirred for 90 minutes and diluted with ether (100 ml.). The suspension obtained was separated by filtration through diatomaceous earth. The residue was washed with ether (50 ml.) and the combined filtrate and washings evaporated. The residual oil was purified by flash column chromatography, eluting with 40% v/v ethyl acetate/hexane to give 1,3-dihydro(5-benzo[c]furyl)carboxaldehyde as a semi-solid mass (0.66 g.); NMR: 9.95 (1H,s); 7.7–7.8 (2H,m); 7.3 (1H d,J=8H) and 5.1 (4H,s)ppm.

EXAMPLES 65–69

Using a similar procedure to that described for Example 33 but starting from the appropriate aldehydes of formula Ra.CHO, the following acids of formula Ib were obtained in yields of 30–80%:

(Example 65): Ra=isopropyl, Rb=H, benzene ring B is unsubstituted; as an oil; NMR: 10.0 (1H, br s), (7.1–7.5) (5H,m), 5.0–5.6 (2H,m), 4.9 (1H,d,J=1Hz), 4.5 (1H,d,J=3Hz), 3.8–4.2 (2H,m), 1.3–2.7 (10H,m) and 1.05 (6H,d,J=8Hz)ppm; m/e: 331 (M$^+$+H); using isobutyraldehyde in place of benzaldehyde at room temperature for 3 days;

(Example 66): Ra=pentyl, Rb=H, benzene ring B is unsubstituted; as an oil; NMR: 7.2–7.4 (5H,m), 5.2–5.5 (2H,m), 4.9 (1H,d,J=2Hz), 4.7 (1H,t,J=3Hz), 3.7–4.2 (2H,m) and 0.7–2.6 (20H,m)ppm; m/e: 359 (M$^+$+H); using hexanal in place of benzaldehyde;

(Example 67): Ra=octyl, Rb=H, benzene ring B is unsubstituted; as an oil; NMR: 7.1–7.4 (5H,m), 5.1–5.5 (2H,m), 4.9 (1H,d, J=1Hz , 4.75 (1H,t, J=3Hz), 3.7–4.2 (2H,m), 1.05–2.6 (23H,m) and 0.85 (3H,br t) ppm; m/e: 403 (M$^+$+H); starting from 1-nonanal in place of benzaldehyde;

(Example 68): Ra=2-chlorophenyl, Rb=H, benzene ring B is 2-fluorophenyl; as an oil; NMR: 1.4–2.8 (9H,m), 4.1–4.3 (2H,m), 5.1–5.5 (3H,m), 6.05 (1H,s), 7.22 (7H,m) and 7.82 (1H,m) ppm; starting from 2-chlorobenzaldehyde and 5(Z)-7-[2,2-dimethyl-4-(2-fluorophenyl)-1,3-dioxan-cis-5-yl]heptenoic acid;

(Example 69): Ra=2-methylphenyl, Rb=H, benzene ring B is 2-methoxyphenyl; as an oil; NMR: 1.4–2.8 (9H,m), 2.44 (3H,s), 3.85 (3H,s), 4.0–4.3 (2H,m), 5.1–5.5 (3H,m), 5.87 (1H,s) and 7.28 (8H,m)ppm; starting from 2-methylbenzaldehyde and 5(Z)-7-[2,2-dimethyl-4-(2-methoxyphenyl)-1,3-dioxan-cis-5-yl]heptenoic acid.

EXAMPLE 70

Using a similar method to that described in Example 4, there was obtained 5(Z)-7-[2,2-diethyl-4-(2-fluorophenyl)-1,3-dioxan-cis-5-yl]heptenoic acid; NMR: 0.7–1.2 (6H,m), 1.3–2.6 (13H,m), 3.7–4.3 (2H,m), 5.1–5.5 (3H,m), 7.11 (3H,m) and 7.52 (1H,m) ppm; as an oil in 54% yield starting from [2,2-diethyl-4-(2-fluorophenyl)-1,3-dioxan-cis-5-yl]acetaldehyde, itself obtained in 64% yield as an oil with IR absorption at 1720 cm$^{-1}$ by oxidation of (4,5-cis)-5-allyl-2,2-diethyl-4-(2-fluorophenyl)-1,3-dioxane. The latter compound showed significant NMR aromatic proton signals at 7.15 (3H,m) and 7.58 (1H,m)ppm and was obtained in 23% yield from erythro-2-allyl-1-(2-fluorophenyl)-1,3-propanediol using an analogous procedure to that described for the corresponding starting material in Example 4, but starting from (4,5-cis)-5-allyl-2,2-diethyl-4-(2-fluorophenyl)-1,3-dioxane.

EXAMPLE 71

In a similar manner to example 1, but starting from [2,2-bis(trifluoromethyl)-4-phenyl-1,3-dioxan-cis-5-yl]acetaldehyde, there was obtained 5(Z)-7-[2,2-bis(trifluoromethyl)-4-phenyl-1,3-dioxan-cis-5-yl]heptenoic acid as a colourless oil in 65% yield; NMR:1.3–2.6 (9H,m), 4.0–4.5 (2H,m), 4.9–5.6 (3H,m) and 7.1–7.5 (5H,m)ppm; m/e: 426 (M$^+$).

The starting material was obtained as follows:

(a) A solution of p-toluenesulphonyl chloride (15.8 g.) in methylene chloride (50 ml.) was added over an hour to a stirred solution of crude erythro-2-allyl-1-phenyl-1,3-propanediol (15.4 g.) in methylene chloride (150 ml.) containing triethylamine (12.0 ml.) and kept at 4° C. The mixture was stirred a further 1 hour at 4° C. and then for 64 hours at room temperature before being diluted with ether (500 ml.). The subsequent mixture was washed successively with water (100 ml.) 5% w/v sodium hydrogen carbonate solution (100 ml.), water (2×100 ml.) and saturated brine solution (100 ml.), then dried (MgSO$_4$) and concentrated to give an oil which on column chromatography, eluting with 10% v/v ethyl acetate/hexane, gave 3-(erythro-2-allyl-1-phenyl-1,3-propanediol) p-toluenesulphonate ester (X), as a colourless oil in 69% yield; NMR: 1.8–2.3 (4H,m), 2.4 (3H,s), 3.7–4.2 (2H,m), 4.7–5.0 (3H,m), 5.35–5.8 (1H,m), 7.2–7.4 (7H,m) and 7.75 (2H, d,J=8Hz)ppm.

(b) A solution of the ester (X) (3.46 g.) in dry ether (10 ml.) containing anhydrous p-toluenesulphonic acid (5 mg.) was added over 10 minutes to a stirred solution of hexafluoroacetone (prepared from 3.0 ml. of the sesquihydrate) at −70° C. The mixture was stirred for 2½ hours at −70° C. and then allowed to warm to room temperature with stirring for 16 hours. The solvent was evaporated and the residual oil dissolved in anhydrous ether (50 ml.) and sodium hydride (0.36 g.) was added in portions. The stirred mixture was heated under reflux for 1 hour, cooled, and treated with ethanol (2 ml.) and ether (50 ml.). This mixture was washed with water (4×15 ml.), dried (MgSO$_4$) and evaporated. The residual oil gave, on column chromatography eluting with 1.5% v/v ethyl acetate/hexane, (4,5-cis)-5-allyl-2,2-bis(trifluoromethyl)-4-phenyl-1,3-dioxane (Y) as a crystalline solid (61%); m.p. 34°–35° C. NMR: 1.6–2.5 (3H, m), 4.1–4.5 (2H,m), 4.8–5.7 (4H,m) and 7.1–7.4 (5H,m) ppm; m/e: 340 (M+).

(c) Ozone was passed through a solution of the dioxane (Y) (1.70 g.) in ethyl acetate (100 ml.) at −78° C. until a permanent blue colour developed. The solution was then flushed with argon until colourless. A solution of triphenylphosphine (1.97 g.) in ethyl acetate (20 ml.) was then added and the mixture was stirred for 1 hour at −78° C. and then overnight at 4° C. This mixture was evaporated and the residue was purified by column chromatography, eluting with 15% v/v ethyl acetate/hexane to give [2,2-bis(trifluoromethyl)-4-phenyl-1,3-dioxan-cis-5-yl]acetaldehyde as a crystalline solid, m.p. 52.5°–53.5° C. in 93% yield; NMR: 2.15–3.1 (3H,m), 4.0–4.7 (2H,m), 5.55 (1H, br s), 7.15–7.55 (5H,m) and 9.55 (1H,s)ppm; m/e: 342 (M+).

EXAMPLES 72–73

In a similar manner to that described in Example 71, there were prepared:

5(Z)-7-([2,4,5-cis]-2-trifluoromethyl-4-phenyl-1,3-dioxane-5-yl)heptenoic acid (Example 72) as a crystalline solid, m.p. 87.5°–88.5° C., in 76% yield; NMR: 1.2–2.7 (9H,m), 3.8–4.3 (2H,m), 4.95–5.6 (4H,m), 7.1–7.4(5H,m) and 9.25 (1H br s) ppm; m/e: 357 (M+ − H); and 5(Z)-7-([2,4-trans,4,5-cis]-2-trifluoromethyl-4-phenyl-1,3-dioxane-5-yl)heptenoic acid (Example 73) as a crystalline solid, m.p. 62°–64° C., in 96% yield; NMR: 1.5–2.6 (9H,m), 3.85–4.5 (2H,m), 5.05–5.6 (4H,m), 7.1–7.5 (5H,m) and 9.85 (1H,br s)ppm; m/e: 358 (M+). The following intermediates were obtained:

(i) [2,4,5-cis]-2-trifluoromethyl-4-phenyl-1,3-dioxan-5-yl)acetaldehyde as an oil in 96% yield; NMR: 2.15–3.2 (3H,m), 4.0–4.2 (2H,m), 5.0–5.2 (2H,m), 7.15–7.5(5H,m) and 9.6 (1H,s)ppm; m/e: 274 (M+); and (ii) ([2,4-trans,4,5-cis]-2-trifluoromethyl-4-phenyl-1,3-dioxan-5-yl)acetaldehyde as a crystalline solid, m.p. 62°–63° C., in 92% yield; NMR: 2.2–3.05 (3H,m), 3.8–4.65 (2H,m), 5.1–5.55 (2H,m), 7.15–7.5 (5H,m) and 9.6 (1H,s)ppm.

These aldehydes were obtained by oxidation of the corresponding 5-allyl-1,3-dioxanes as described for example 71. These dioxanes were obtained together by substituting trifluoroacetaldehyde for hexafluoroacetone in procedure (b) of Example 71, followed by chromatographic separation on silica using 2% v/v ethyl acetate/hexane as eluant, resulting in the isolation of:

(iii) [2,4,5-cis]-5-allyl-2-trifluoromethyl-4-phenyl-1,3-dioxane in 49% yield as a crystalline solid, m.p. 60°–61° C.; NMR: 1.6–1.95 (2H,m), 2.1–2.6 (1H,m), 3.9–4.4 (2H,m), 4.8–5.15 (4H,m), 5.3–5.8 (1H,m) and 7.2–7.4 (5H,m)ppm; m/e: 272 (M+); and (iv) [2,4-trans,4,5-cis]-5-allyl-2-trifluoromethyl-4-phenyl-1,3-dioxane in 15% yield as a crystalline solid m.p. 78°–79° C.; NMR: 1.65–2.45 (3H,m), 3.9–4.5 (2H,m), 4.8–5.8 (5H,m) and 7.25–7.45 (5H,m) ppm; m/e: 272 (M+).

EXAMPLE 74

To a solution of methyl 5(Z)-7-([2,4,5-cis]-2-chloromethyl-4-phenyl-1,3-dioxan-5-yl)heptenoate (300 mg.) in methanol (10 ml.) was added aqueous potassium hydroxide (2M,2.6 ml.). The mixture was stirred for 4½ hours and diluted with water (50 ml.), then extracted with ether (2×20 ml.) and the extracts discarded. The aqueous layer was acidified to pH 5 (2M hydrochloric acid) and extracted with ether (3×20 ml.). The extracts were dried (MgSO$_4$) and evaporated to give an oil which on column chromatography, eluting with 85:12:2 (by volume) toluene/ethyl acetate/acetic acid gave 5(Z)-7-([2,4,5-cis]-2-chloromethyl-4-phenyl-1,3-dioxan-5-yl)heptenoic acid in 92% yield as a crystalline solid; m.p. 58°–61° C.; NMR: 1.4–2.7 (9H,m), 3.65 (2H,d, J=4 Hz), 3.85–4.3 (2H,m), 4.85–5.55 (4H,m), 7.2–7.4 (5H,m) and 8.4 (1H,br s)ppm.

EXAMPLE 75

A solution containing methyl 5(Z)-erythro-9-hydroxy-8-hydroxymethyl-9-phenylnonenoate (584 mg.), p-toluenesulphonic acid (10 mg.) and 2-chloro-1,1-dimethoxyethane (2 ml.) was heated at 100° C. for 18 hours. The cooled reaction mixture was diluted with ether (80 ml.) and successively washed with 5% w/w sodium hydrogen carbonate solution (2×10 ml.), water (3×10 ml.) and saturated sodium chloride solution (1×10 ml.), then dried (MgSO$_4$) and evaporated to give an oil, which on column chromatography, using 2% v/v ethyl acetate/toluene as eluant, gave methyl 5(Z)-7-(2,4,5-cis]-2-chloromethyl-4-phenyl-1,3-dioxan-5-yl)heptenoate as a colourless oil in 52% yield; NMR: 1.4–2.65 (9H,m), 3.6–3.8 (5H,m), 3.8–4.25 (2H,m), 4.85–5.55 (4H,m) and 7.2–7.45 (5H,m) ppm; m/e: 351 (M+ − H).

The starting material was obtained as follows:

An ethereal solution of diazomethane was added to a solution of 5(Z)-erythro-9-hydroxy-8-hydroxymethyl-9-phenylnonenoic acid (3.99 g.) in dry ether (50 ml.) at 4° C., until a yellow colour persisted in the mixture. A few drops of acetic acid were then added until effervescence had ceased. The mixture was evaporated to give an oil which on column chromatography using 70:30:2 (by volume) toluene/ethyl acetate/acetic acid as eluant, gave methyl 5(Z)-erythro-9-hydroxy-8-hydroxymethyl-9-phenylnonenoate as a colourless oil in 81% yield; NMR: 1.4–2.4 (9H,m) 2.6–3.1 (2H,br s), 3.55–3.8 (5H,m), 4.9–5.55 (3H,m) and 7.15–7.45 (5H,m)ppm.

EXAMPLES 76-79

Using a similar procedure to that described in Example 74, the following compounds were obtained by hydrolysis of the corresponding methyl esters:

(Example 76): 5(Z)-7-([2,4,5-cis]-2-chloroethyl-4-phenyl-1,3-dioxan-5-yl)heptenoic acid as a crystalline solid, m.p. 54°–54.5° C. in 92% yield; NMR:1.4–2.6 (11H,m), 3.75 (2H,t,J=7Hz), 3.8–4.2 (2H,m), 4.9–5.55 (4H,m), 7.2–7.4 (5H,m) and 9.8 (1H,br s) ppm;

(Example 77): 5(Z)-7-(4'-phenyl-[4-methylcyclohexanespiro-2'-1,3-dioxan]-cis-5'-yl)heptenoic acid (isomer A*) as a colourless oil in 81% yield; NMR: 0.7–2.9 (21H,m), 3.6–4.2 (2H,m), 4.9–5.6 (3H,m) and 7.1–7.5 (5H,m)ppm; m/e: 372 (M+); and (Example 78): 5(Z)-7-(4'-phenyl-[4-methylcyclohexanespiro-2'-1,3-dioxan]-cis-5'-yl)heptenoic acid (isomer B*) as a colourless oil in 53% yield; NMR: 0.7–2.9 (21H,m), 3.6–4.4 (2H,m), 5.0–5.5 (3H,m) and 7.1–7.5 (5H,m)ppm; m/e: 372 (M+); [* Isomers A and B were obtained, respectively, by hydrolysis of the less polar and more polar isomers of methyl 5(Z)-7-(4'-phenyl-[4-methylcyclohexanespiro-2'-1,3-dioxan]-cis-5'-yl)heptenoate, as seen on TLC analysis in 10% v/v ethyl acetate/hexane.]

(Example 79): 5(Z)-7-([2,4,5-cis]-2-vinyl-4-phenyl-1,3-dioxan-5-yl)heptenoic acid as a solid, m.p. 40°–43° C., in 80% yield; NMR: 1.4–2.7 (9H,m), 3.8–4.3 (2H,m), 5.05 1H,d,J=3Hz), 5.1–5.55 (4H,m), 5.6–5.7 (1H,m), 5.8–6.3 (1H,m), 7.2–7.4 (5H,m) and 7.7 (1H,br s)ppm; m/e: 316 (M+).

EXAMPLES 80-82

Using a similar procedure to that described in Example 75, the following esters were obtained from methyl 5(Z)-erythro-9-hydroxy-8-hydroxymethyl-9-phenyl-nonenoate:

(Example 80): methyl 5(Z)-7-([2,4,5-cis]-2-chloroethyl-4-phenyl-1,3-dioxan-5-yl)heptenoate as a colourless oil in 63% yield; NMR: 1.4–2.6 (11H,m), 3.55–4.3 (7H,m), 4.85–5.5 (4H,m) and 7.15–7.45 (5H,m)ppm; by replacing 2-chloro-1,1-dimethoxyethane with 3-chloro-1,1-dimethoxypropane, carrying out the reaction at room temperature for 16 hours, and purification by column chromatography on silica using 10% v/v ethyl acetate/hexane as eluant;

(Example 81): methyl 5(Z)-7-(4'-phenyl-[4-methylcyclohexanespiro-2'-1,3-dioxan]-cis-5'-yl)heptenoate (less polar isomer on TLC: SiO2, 10% v/v ethyl acetate/hexane), as a colourless oil in 38% yield; NMR: 0.9 (3H,d), 1.0–2.7 (18H, m), 3.6 (3H,s), 3.8 (1H,m), 4.05 (1H,m), 5.1–5.4 (3H,m) and 7.1–7.4 (5H,m)ppm;

(Example 82): methyl 5(Z)-7-(4'-phenyl-[4-methylcyclohexanespiro-2'-1,3-dioxan]-cis-5'-yl)heptenoate (more polar isomer on TLC: SiO2, 10% v/v ethyl acetate/hexane) as a colourless oil in 28% yield; NMR: 0.9 (3H,d), 1.0–2.7 (18H,m), 3.6 (3H,s), 3.7 (1H,d), 4.2 (1H,d), 5.15 (1H,d), 5.2 (1H,m), 5.3 (1H,m) and 7.2–7.4 (5H,m)ppm;

[Both Example 81 and 82 were obtained in the same reaction by replacing 2-chloro-1,1-dimethoxyethane with 4-methylcyclohexanone (0.27 ml.) and trimethyl orthoformate (0.29 ml.), carrying out the reaction at room temperature for 2 hours, and purifying the crude product by column chromatography using 10% v/v ethyl acetate/hexane as eluant.].

EXAMPLE 83

A solution containing 5(Z)-erythro-9-hydroxy-8-hydroxymethyl-9-phenylnonenoate (222 mg.), p-toluenesulphonic acid (5 mg.) and 3,3-dimethoxy-1-propene (0.2 ml.) in toluene (1 ml.) was stirred for 3 hours. Water (20 ml.) was added and the mixture was extracted with ether (3×10 ml.). The combined organic extracts were washed successively with water (2×10 ml.) and saturated brine solution (1×50 ml.), dried (MgSO4) and evaporated to give an oil which on column chromatography, using 20% v/v ethyl acetate/hexane as eluant, gave methyl 5(Z)-7-([2,4,5-cis]-2-vinyl phenyl-1,3-dioxan-5-yl)heptenoate as a colourless oil in 48% yield, essentially pure by TLC analysis.

EXAMPLE 84

A solution containing 5(Z)-erythro-9-hydroxy-8-hydroxymethyl-9-(2-methylphenyl)nonenoic acid (2.75 g.) and powdered potassium hydroxide (4.19 g.) in dimethyl sulphoxide (23 ml.) was treated with dibromomethane (3.26 g.) with stirring under argon. Stirring was continued overnight. The mixture was then poured into ice-water (70 ml.), acidified to pH5 (2M hydrochloric acid), and extracted with ethyl acetate (3×50 ml.). The combined extracts were washed with water and saturated brine, dried (MgSO4) and evaporated to give an oil (2.8 g.) which was purified by column chromatography using 80:20:2 by (volume) toluene/ethyl acetate/acetic acid to give 5(Z)-(4-[2-methylphenyl]-1,3-dioxan-cis-5-yl)heptenoic acid (1.0 g.) as an oil which solidified on standing to give a crystalline solid, m.p. 83°–86° C.; NMR: 7.1–7.5 (4H,m), 4.9–5.4 (5H,m), 3.8–4.1 (2H,m), 1.5–2.65 (9H,m) and 2.25 (3H,s)ppm.

EXAMPLE 85

A solution containing sodium ethoxide (from sodium metal, 0.095 g.) in ethanol (20 ml.) was treated with a solution of 5(Z)-7-(2,2-dimethyl-4-phenyl-1,3-dioxan-cis-5-yl)heptenoic acid (0.12 g.) in ethanol (20 ml.) and the mixture was stirred for 2 hours. The solvent was evaporated to leave a white powder which on crystallisation from dichloromethane/hexane gave sodium 5(Z)-7-(2,2-dimethyl-4-phenyl-1,3-dioxan-cis-5-yl)heptenoate as white crystals, m.p. 160°–169° C. (decomposition),; microanalysis found: C,66.1; H,7.5%; Calculated ($C_{19}H_{25}O_4Na+\frac{1}{4}H_2O$):C,66.2;H,7.4%.

EXAMPLE 86-92

A solution containing 5(Z)-7-(2,2-dimethyl-4-phenyl-1,3-dioxan-cis-5-yl)heptenoic acid (318 mg.), 4-dimethylaminopyridine (122 mg.) and methanesulphonamide (95 mg.) in dry dichloromethane (20 ml.) was treated with a solution of dicyclohexylcarbodiimide (206 mg.) in dichloromethane (2 ml.). The mixture was stirred overnight, filtered, and the filtrate was evaporated. The residual oil was partitioned between saturated aqueous sodium carbonate solution (50 ml.) and ether (50 ml.), and the aqueous phase was washed with more ether (2×25 ml.). The aqueous phase was acidified with hydrochloric acid (2M) and extracted with ethyl acetate (3×25 ml.). The combined extracts were washed with saturated brine, dried (MgSO4) and evaporated to give an oil which on column chromatography, eluting with toluene/ethyl acetate/acetic acid (80:20:2 v/v) gave N-methanesulphonyl-5(Z)-7-(2,2-dimethyl-4-phenyl-1,3-dioxan-cis-5-yl)heptenamide, as a colourless oil (100 mg.); NMR: 1.2–2.5 (9H,m), 1.55 (6H,s), 3.25 (3H,s), 3.7–4.3 (2H,m), 5.1–5.5 (3H,m), 7.1–7.4 (5H,br.s) and 8.4 (1H,br s)ppm.

Using a similar procedure the following N-alkanesulphonyl heptenamides may be obtained starting from the appropriate heptenoic acid of formula Ib:

(Example 87): N-methanesulphonyl-5(Z)-7-(4-phenyl-1,3-dioxan-cis-5-yl)heptenamide, as a solid, m.p. 85°–87° C. in 71% yield; NMR: 1.2–2.5 (9H,m), 3.25 (3H,s), 3.7–4.3 (2H,m), 4.8–5.5 (5H, m), 7.1–7.4 (5H,br s) and 8.4 (1H, br s)ppm; m/e: 368 (M+ +H);

(Example 88): N-methanesulphonyl-5(Z)-7-(2,2-diethyl-4-phenyl-1,3-dioxan-cis-5-yl)heptenamide, as an oil in 70% yield; NMR: 0.7–1.3 (6H,m), 1.2–2.5 (13H,m), 3.25 (3H,s), 3.7–4.3(2H,m), 5.1–5.5 (3H,m), 7.1–7.4 (5H,br s) and 8.5 (1H, br s )ppm; m/e 424 (M+ +H);

(Example 89): N-ethanesulphonyl-5(Z)-7-[4-(2-fluorophenyl)-2,2-dimethyl-1,3-dioxan-cis-5-yl]heptenamide, as an oil in 77% yield; NMR: 1.35 (3H,t), 2.15 (15H,m), 3.45 (2H,q), 4.03 (2H,m), 5.34 (3H,m), 7.12 (4H,m) and 7.50 (1H,m)ppm; m/e: 428 (M+ +H);

(Example 90): N-ethanesulphonyl-5-(Z)-7-[4-(2-ethylphenyl)-2,2-dimethyl-1,3-dioxan-cis-5-yl]heptenamide, as an oil in 74% yield; NMR: 1.32 (6H,m), 1.64 (8H,m), 2.33 (9H,m), 3.46 (2H,q), 4.07 (2H,m), 5.30 (3H,m), 7.23 (4H,m) and 7.50 (1H,m)ppm; m/e: 438 (M+ +H);

(Example 91): N-methanesulphonyl-5(Z)-7-[4-(2-ethylphenyl)-2,2-dimethyl-1,3-dioxan-cis-5-yl]heptenamide, as an oil in 81% yield; NMR: 1.13 (3H,t), 2.05 (17H,m), 3.16 (1H,s), 3.83 (2H,m), 5.15 (3H,m), 7.1 (4H,m) and 7.37 (1H,m)ppm; m/e: 424 (M+ +H);

(Example 92) N-(1-methylethanesulphonyl)-5(Z)-[4-(2-ethylphenyl)-2,2-dimethyl-1,3-dioxan-cis-5-yl]heptenamide, as an oil in 73% yield; NMR: 1.4 (15H,m), 2.27 (11H,m), 3.83 (3H,m), 5.18 (3H,m), 7.10(4H,m) and 7.46 (1H,m)ppm; m/e: 452 (M+ +H).

EXAMPLE 93

A solution containing erythro-9-hydroxy-8-hydroxymethyl-9-phenylnonanoic acid (250 mg.), 2,2-dimethoxypropane (93 mg.) and p-toluenesulphonic acid (3 mg.) in dry THF (10 ml.) was stirred for 30 minutes and then allowed to stand overnight. Triethylamine (2 drops) was added and the mixture was partitioned between ether (50 ml.) and water (50 ml.). The organic layer was washed with saturated brine (20 ml.), dried (MgSO4) and evaporated to give an oil. Column chromatography, eluting with 80:20:2 (by volume) toluene/ethyl acetate/acetic acid gave 7-(2,2-dimethyl-4-phenyl-1,3-dioxan-cis-5-yl)heptanoic acid (180 mg.) as a colourless oil; NMR: 1.55 (6H,d), 0.9–2.4 (13H,m), 3.7–4.3 (2H,m), 5.15 (1H,br s) and 7.3 (5H,br s )ppm.

The starting material was obtained as follows:

Hydrogenation of a solution of 5(Z)-erythro-9-hydroxy-8-hydroxymethyl-9-phenylnonenoic acid (320 mg.) in ethyl acetate (20 ml.) using Adam's catalyst (30 mg.) for 2 hours at atmospheric pressure, followed by filtration and evaporation gave erythro-9-hydroxy-8-hydroxymethyl-9-phenylnonanoic acid (317 mg.) as an oil, which was essentially pure by TLC analysis and was used without characterisation.

EXAMPLE 94

A portion (2.1 ml.) of a 0.5M solution of sodium thioethoxide in N,N-dimethylformamide was added under nitrogen to 5(Z)-7-[2,2-dimethyl-4-(2-methoxyphenyl)-1,3-dioxan-cis-5-yl]heptenoic acid (104 mg.). The mixture was heated under reflux for 1.1 hours and then diluted with ice-water to a total volume of 25 ml. The aqueous mixture was acidified to pH 4 with acetic acid and extracted with ethyl acetate (2×15 ml.). The extracts were washed with saturated brine, dried (MgSO4) and evaporated. The oil obtained was purified by column chromatography on silica (12 g.) eluting with 80:20:2 (by volume) toluene/ethyl acetate/acetic acid to give 5(Z)-7-[2,2-dimethyl-4-(2-hydroxyphenyl)-1,3-dioxan-cis-5-yl]heptenoic acid as an oil (25 mg.); NMR: 1.50 (6H,s), 2.22 (9H,m), 3.97 (2H,m), 5.31 (3H,m), 6.98 (4H,m) and 8.38 (2H,s)ppm.

EXAMPLE 95

Potassium t-butoxide (7.4 g.) was added to a stirred mixture of (4-carboxybutyl)triphenyl phosphonium bromide (14.7 g.) and THF (170 ml.) at 0°–5° C. under nitrogen. This mixture was added dropwise during 10 minutes to a stirred solution of (2,2-dimethyl-4-phenyl-1,3-dioxan-cis-5-yl)acetaldehyde (3.1 g.) in THF (50 ml.) at 0°–5° C. The mixture was stirred for 18 hours, poured onto ice (400 g.) and the solvent evaporated. The aqueous residue was washed with ethyl acetate and insoluble material removed by filtration through diatomaceous earth. The filtrate was cooled to 0° C. and acidified to pH4 by addition of a saturated solution of sodium hydrogen tartrate (160 ml.). The resultant emulsion was extracted with a 1:1 v/v mixture of ether and pentane.

The combined extracts were washed with saturated brine, dried (Na2SO4) and evaporated to give an oil which was purified by chromatography using a 3:1 v/v mixture of hexane and ether as eluant to give 5(Z)-7-(2,2-dimethyl-4-phenyl-1,3-dioxan-cis-5-yl)heptenoic acid as an oily solid (2.6 g.) m p. 79°–85° C. (2.6 g.), which was crystallised from hexane (3 times) to give material of m.p. 86°–86.5° C.; $^1$H-NMR: 1.55 (6H,s), 1.4–2.7 (9H,m), 3.80 (1H,dd), 4.15 (1H,br d), 5.0–5.5 (3H,m), 7.30 (5H,s) and 11.0 (1H,br s )ppm; and $^{13}$C-NMR (CDCl3,22.5 MHz): 19.02 (axial CH3), 21.67 (C7*,cis), 24.49 (C3*), 26.28 (C4*,cis), 29.64 (equatorial CH3), 33.37 (C2*), 39.66 (dioxan-C5), 62.52 (dioxan-C6), 73.08 (dioxan-C4), 76.93 (CDCl3), 98.98 (dioxan-C2), 125.31 (phenyl-C2), 126.72 (phenyl-C4), 127.96 (phenyl-C3), 128.99 (C6*), 130.18 (C5*), 140.80 (phenyl-C1) and 179.05 (C1*,CO2H)ppm (relative to TMS). [*refer to heptenoic acid carbon atoms]; i.e. essentially free from 5(E) isomer.

The starting aldehyde was obtained as follows:

A solution of osmium tetroxide (47 mg.) in water (6.0 ml.) was added to a stirred solution of (4,5-cis)-5-allyl-4-phenyl-1,3-dioxane (3.6 g.) in THF (160 ml.). When the solution had become brown (5 minutes), it was treated dropwise during 30 minutes with a solution of sodium periodate (13.7 g.) in water (90 ml.). The mixture was further stirred for 2 hours and the solid removed by filtration. The filter cake was washed first with THF (15 ml.) and then with hexane (200 ml.). The aqueous phase of the filtrate was washed with hexane and the hexane washings combined with the organic phase of the filtrate. The solution obtained was concentrated in vacuo to low volume and the residual material diluted with further hexane. The solution obtained was washed with 10% w/v sodium sulphide solution, then with saturated brine and then dried (Na2SO4) and evaporated. The residual oil was purified by column chromatography using 1:1 v/v hexane and ether as eluant. There was thus obtained (2,2-dimethyl-4-phenyl-1,3-dioxan-cis-5-yl)acetaldehyde as a solid, m.p. 69°–70° C.

(after recrystallisation from hexane); NMR: 1.56 (6H,s), 2.09–2.45 (2H,m), 2.87 (1H,m), 3.80 (1H,dd), 4.33 (1H,dt), 5.24 (1H,d), 7.33 (5H,s) and 9.59 (1H,s)ppm.

EXAMPLES 96–97

Using a similar procedure to that described in Example 95, but starting from (+)-(2,2-dimethyl-4-phenyl-1,3-dioxan-cis-5-yl)acetaldehyde, there was obtained (+)-5(Z)-7-(2,2-dimethyl-4-phenyl-1,3-dioxan-cis-5-yl)heptenoic acid (Example 96 ) as a syrup in 62% yield, $[\alpha]_D^{20}+99.5°$(c,4.00, MeOH), having an identical NMR spectrum to that described for the racemic form in Example 95, and containing approximately 4% of the 5(E) isomer as judged by $^{13}$C-NMR spectroscopy.

Similarly, (−)-5(Z)-7-(2,2-dimethyl-4-phenyl-1,3-dioxan-cis-5-yl)heptenoic acid (Example 97) was obtained as a syrup in 65% yield, $[\alpha]_D^{20}+101°$ (c, 4.24, MeOH), having an identical NMR spectrum to that described for the racemic form in Example 95, and containing about 5% of the 5(E) isomer by $^{13}$C-NMR spectroscopy, starting from (−)-(2,2-dimethyl-4-phenyl-1,3-dioxan-cis-5-yl)acetaldehyde.

The starting enantiomeric aldehydes were obtained as follows:

(i) A solution of recrystallised (±)-(2,2-dimethyl-4-phenyl-1,3-dioxan-cis-5-yl)acetaldehyde (14.0 g., m.p. 69°–70° C.) and (−)-ephedrine (9.9 g.) in benzene (200 ml.) was heated under reflux for 2.5 hours using a Dean and Stark apparatus for azeotropic removal of water. The solution was then evaporated and the residual oil triturated with hexane to give solid which was recrystallised from hexane and petroleum ether (b.p. 30°–40° C.) to give (−)-[2,4,5-cis]-3,4-dimethyl-2-[(2,2-dimethyl-4-phenyl-1,3-dioxan-cis-5-yl)methyl]-5-phenyloxazolidine (A) as a crystalline solid (5.9 g.), m.p. 104°–105° C., $[\alpha]_D^{20}-46°$ (c,4.23, acetone); microanalysis, found: C, 75.5; H,8.3; N,3.7%; $C_{24}H_{31}NO_3$ requires: C, 75.5; H,8.2; N,3.7%; m/e: 382 (M+ +H).

(ii) A solution of anhydrous (+)-tartaric acid (2.98 g.) in acetone (299 ml.) containing 1% v/v of water was added to a solution of the (−)-enantiomer (A, above) (7.6 g.) in acetone (50 ml.). The mixture was stirred for 18 hours and the precipitate of ephedrine tartrate separated by filtration. The residue was washed with acetone and the combined washings and filtrate were evaporated. This residue was partitioned between ether and water. The ethereal phase was dried ($Na_2SO_4$) and evaporated. The resultant oil was purified by column chromatography using 3:1 v/v hexane and ether as eluant. There was thus obtained (−)-(2,2-dimethyl-4-phenyl-1,3-dioxan-cis-5-yl)acetaldehyde as a syrup (4.3 g.), $[\alpha]_D^{20}-58°$ (c, 4.20, MeOH), having an NMR spectrum identical with that described for the racemic aldehyde in Example 95.

(iii) Using a similar procedure to (i) above but using (+)-ephedrine and starting from 12.9 g. of the racemic aldehyde, there was obtained (+)-[2,4,5-cis]-3,4-dimethyl-2-[(2,2-dimethyl-4-phenyl-1,3-dioxan-cis-5-yl)methyl]-5-phenyloxazolidine (B) as a crystalline solid (4.5 g.) m.p. 104°–105° C., $[\alpha]_D^{20}+46°$ (c,4.02, acetone); microanalysis, found: C,75.9; H,8.0; N,3.8%; $C_{24}H_{31}NO_3$ requires: C, 75.5; H,8.2; N, 3.7%; m/e: 382 (M+ +H).

(iv) Using a similar procedure to (ii) above but using (+)-tartaric acid and the (+)-enantiomer (B, above) (7.9 g.), there was obtained (+)-(2,2-dimethyl-4-phenyl-1,3-dioxan-cis-5-yl)acetaldehyde as a syrup (4.4 g.), $[\alpha]_D^{20}+57°$ (c, 4.20, MeOH), having an NMR spectrum identical with that described for the racemic aldehyde in Example 95.

EXAMPLES 98–99

A solution of (±)-5(Z)-7-(2,2-dimethyl-4-phenyl-1,3-dioxan-cis-5-yl)heptenoic acid (6.0 g., m.p. 84°–84.5° C.) and (−)-α-methylbenzylamine (1.14 g.) in ether (100 ml.) was seeded with crystals of salt X (see below). The crystals which separated were collected by filtration and the mother liquor (A) retained.

The crystals, $[\alpha]_D^{21}+45°$ C. (c,3.08,MeOH) were recrystallised by dissolution in the minimum volume of boiling methanol followed by addition of ether (30 ml.)/g. of crystals). After four recrystallisations pure salt X was obtained as needles (B) (1.6 g.) of constant specific rotation $[\alpha]_D^{20}+68.8°$ (c,3.14,MeOH) and m.p. 123°–128° C. The recrystallisation mother liquors gave further crops of salt X of varying purity $[\alpha]_D^{20}+44$ to +68° ) and mother liquors (C).

The combined mother liquors (A) and (C) were evaporated. The residue was dissolved in the minimum volume of cold methanol. The solution obtained was diluted with ether, washed three times with McIlvaine buffer of pH 4.0, five times with water, dried ($Na_2SO_4$) and evaporated. The residual oily solid [4.0 g., $[\alpha]_D^{20}-29.9°$ (c,3.60, MeOH)] was dissolved in ether (100 ml.) containing (+)-α-methylbenzylamine (1.0 g.). The solution was seeded with salt Y (see below). The crystals [3.2 g., $[\alpha]_D^{21}-55.3°$ (c, 3.05, MeOH], which separated were recrystallised four times as described for salt X above to give pure salt Y as needles (D) 1.72 g. of constant specific rotation $[\alpha]_D^{20}-68.7°$ C. (c,3.10, MeOH) and m.p. 123°–128° C.

Needles D (1.7 g., salt Y) were dissolved in the minimum volume of methanol and the solution diluted with ether. The solution was then washed three times with McIlvaine buffer of pH 4.0, five times with water, dried ($Na_2SO_4$) and evaporated. A solution of the residue in pentane (15 ml.) was then percolated through silica (0.6 g.). The filtrate and washings were combined and evaporated to give (−)-5(Z)-7-(2,2-dimethyl-4-phenyl-1,3-dioxan-cis-5-yl)heptenoic acid (Example 98) as a syrup (1.02 g.), $[\alpha]_D^{20}-105°$ (c,3.99, MeOH), having an identical NMR spectrum with that of the racemic acid described in Example 95.

Similar treatment of needles B (1.6 g., salt X) yielded (+)-5(Z)-7-(2,2-dimethyl-4-phenyl-1,3-dioxan-cis-5-yl)heptenoic acid (Example 99) as a syrup (0.95 g), $[\alpha]_D^{20}+106°$ (c, 4.1, MeOH), having an identical NMR spectrum to that of the racemic acid described in Example 95.

The starting seed crystals were obtained as follows:

A solution the (+)-acid (Example 96) (163 mg.) and (−)-α-methylbenzylamine (62 mg.) in ether (2 ml.) deposited the corresponding salt X as prisms (201 mg.), m.p. 123°–128° C. (indefinite), $[\alpha]_D^{20}+67.8°$ (c, 3.17, MeOH).

Similarly, a solution of the (−)-acid (Example 97) (187 mg.) and (+)-α-methylbenzylamine (71 mg.) in ether (2 ml.) deposited the corresponding salt Y as prisms (221 mg.), m.p. 123°–128° C. (indefinite), $[\alpha]_D^{20}-67.9°$ (c, 2.78, MeOH).

EXAMPLES 100–101

A mixture of (−)-5(Z)-erythro-9-hydroxy-8-hydroxymethyl-9-phenylnonenoic acid (1.2 g.), 3,3-diethoxypentane (5 ml.), and p-toluenesulphonic acid monohydrate (one crystal) was stirred for 18 hours. The mixture was diluted with ether, treated with triethylamine (2 drops) and evaporated in vacuo. An ethereal solution of the residue was washed three times with water, dried ($Na_2SO_4$) and evaporated to give an oil (1.4 g.). This was chromatographed on silica. Elution of the column with mixtures of hexane and ether (10:1 to 3:1) yields (−)-5(Z)-(2,2-diethyl-4-phenyl-1,3-dioxan-cis-5-yl)heptenoic acid (Example 100) as an oil (0.68 g.), $[\alpha]_D^{20}$−82.5° (c, 4.22, MeOH) (containing 2.8% of the corresponding 5(E)isomer by $^{13}C$ NMR spectroscopy); $^1$H-NMR:0.86 (3H,s), 1.08 (3H,s), 1.45–1.95 (1OH,m), 2.23 (2H,t), 2.45 (1H,m), 3.80 (1H,dd), 4.13 (1H,br d), 5.10 (1H,d), 5.02–5.52 (2H,m), 7.32 (5H,s) and 10.05 (1H, br s )ppm.

Using a similar procedure starting from (+)-5(Z)-erythro-9-hydroxy-8-hydroxymethyl-9-phenylnonenoic acid (0.6 g.) there was obtained (+)-5(Z)-(2,2-diethyl-4-phenyl-1,3,-dioxan-cis-5-yl)heptenoic acid (Example 101) as an oil (0.4 g.), $[\alpha]_D^{20}$+82.7° (c,4.26, MeOH) (containing less then 3% of the corresponding 5(E) isomer by $^{13}$C-NMR spectroscopy) and having an essentially identical $^1$H-NMR spectrum to that of Example 100 above.

The necessary starting materials were obtained as follows:

(i) A solution of (−)-5(Z)-7-(2,2-dimethyl-4-phenyl-1,3-dioxan-cis-5-yl)heptenoic acid (1.45 g.) in a mixture of THF (45 ml.) and 1M hydrochloric acid (1.1 ml.) was left at ambient temperature for 18 hours and then evaporated. An ethereal solution of the residue was washed repeatedly with water until no ionic chloride was present in the washings, dried ($Na_2SO_4$) and evaporated to give (−)-5-(Z)-erythro-9-hydroxy-8-hydroxymethyl-9-phenylnonenoic acid as a syrup (1.23 g.) $[\alpha]_D^{20}$−32° (c, 2.14, methanol). $^1$H-NMR: 1.4–2.2 (7H,m), 2.86(2H,t, J-7 Hz), 3.68 (2H,d), 4.8 (3H, br), 4.99 (1H,d, J=3.6 Hz), 5.2–5.6 (2H,m) and 7.33 (5H,s)ppm.

(ii) In a similar manner but starting from (+)-5(Z)-7-(2,2-dimethyl-4-phenyl-1,3-dioxan-cis-5-yl)heptenoic acid (1.26 g.), there was obtained (+)-5(Z)-erythro-9-hydroxy-8-hydroxymethyl-9-phenylnonenoic acid as a syrup (1.1 g.), $[\alpha]_D^{20}$+32° (c, 2.16, MeOH), having an essentaily identical $^1$H-NMR spectrum to that of the (−) isomer in (i) above.

The above procedures were also used to obtain the racemic (±) form of 5(Z)-(2,2-diethyl-4-phenyl-1,3-dioxan-cis-5-yl)heptenoic acid having an identical $^1$H-NMR spectrum to that of the (−)- or (+)- enantiomers (Examples 100,101), starting from racemic 5(Z)-erythro-9-hydroxy-8-hydroxymethyl-9-phenylnonenoic acid.

EXAMPLE 102

A solution of 5(Z)-7- [2,4,5-cis]-2-methyl-4-phenyl-1,3-dioxan-cis-5-yl)heptenoic acid (500 mg.) in absolute ethanol (10 ml.) containing 5% w/w palladium on charcoal catalyst (100 mg.) was stirred under an atmospheric pressure of hydrogen for 3 hours. The catalyst was separated by filtration through kieselguhr and the filtrate was evaporated to give 7-[2,4,5-cis]-2-methyl-4-phenyl-1,3-dioxan-cis-5-yl)heptenoic acid as a colourless oil in 99% yield; NMR: 0.8–1.8 (14H,m), 2.2 (2H,t,J=8Hz), 3.8–4.25 (2H,m), 4.75–5.0 (2H,m), 7.14–7.4 (5H,m) and 8.5–9.3 (1H,br)pm; m/e: 307 ($M^+$+H).

EXAMPLE 103

Aqueous potassium hydroxide (34 ml. of 40% w/v solution) was added to a stirred solution of 5(E)-7-(2,2-dimethyl-4-phenyl-1,3-dioxan-cis-5-yl)heptenonitrile (831 mg.) in freshly distilled ethylene glycol (34 ml.) under an argon atmosphere and the mixture heated under reflux for 3.5 hours. The cooled mixture was diluted with water (100 ml.) and methylene chloride (100 ml.), and then stirred and acidified to pH5 (2M hydrochloric acid). The organic phase was separated, dried ($MgSO_4$) and evaporated. The residue was purified by flash chromatography eluting with 1:99 v/v acetic acid and ethyl acetate to give 5(E)-7-(2,2-dimethyl-4-phenyl-1,3-dioxan-cis-5-yl)heptenoic acid as an oil (454 mg.): $^1$H-NMR: 8.7–9.6 (1H,br,$CO_2H$)m 7.0–7.5 (5H,m), 4.85–5.5 (3H,m), 4.0 (2H,q, J=12Hz) and 1.35–2.55 (15H,m; including s at 1.52 and 1.54)ppm; $^{13}$C-NMR: ($CDCL_3$; 22.5 MHz) 178.94 (Cl*), 140.80 (Ph,Cl), 130.78 (C5*), 129.70 (C6*), 128.02 (C6*), 128.02 (Ph,C3), 126.77 (Ph,C4), 125.42 (Ph,C2), 99.03 (dioxane, C2), 78.39+76.93+75.52 ($CDCl_3$), 73.08 (dioxane, C4), 62.63 (dioxane, C6), 39.55 (dioxane, C5), 33.21 (C2*), 31.70 (C4*), 29.58 (equatorial $CH_3$), 27.09 (C7*), 24.38 (C3* and 19.13 (axial $CH_3$) ppm [Note: asterisk values refer to the heptenoic acid moiety]; m/e: 318 ($M^+$), 303 (M-$CH_3$) and 260 [M-($CH_3$)$_2$CO].

The starting material was obtained as follows:

A solution of 2-(2,2-dimethyl-4-phenyl-1,3-dioxan-cis-5-yl)acetaldehyde (518 mg.) in dry THF (10 ml.) was added over 30 minutes to a stirred solution of vinyl magnesium bromide (3,4 ml of 1,3M solution in tetrahydrofuran) in tetrahydrofuran (5 ml.), at 0° C. under an atmosphere of Argon. After further stirring at 0° C. for 1 hr, saturated ammonium chloride solution was added to quench the reaction. The mixture obtained was separated and the aqueous phase was extracted with ether. The combined organic phases were dried ($MgSO_4$) and evaported. The residue was purified by flash chromatography, eluting with 1:1 v/v ethyl acetate/hexane to give an epimeric mixture of 3-hydroxy-4-(2,2-dimethyl-4-phenyl-1,3-dioxan-cis-5-yl)-but-1-ene (A), as an oil (564 mg.) NMR: 7.3 (5H,s); 5.35–5.9 (1H,m); 4.8–5.3 (3H,m); and 0.8–2.2 (1OH,m), including 2 s at 1.55 m+OH)ppm.

Propionic acid (7.4 micromole) was added to a solution of (A; 433 mg.) in trietyl orthoacetate (2.2 ml.). The mixture was stirred at 140°–145° C. with removal of ethanol by distillation during 1 hour. The cooled reaction mixture was evaporated and the residue purified by flash chromatography, eluting with 15:85 v/v ethyl acetate/hexane to give ethyl 4(E)-6-(2,2-dimethyl-4-phenyl-1,3-dioxan-cis-5-yl)hexenoate (B) as an oil (329 mg.); NMR: 7.3 (5H,s), 5.1–5.5 (3H,m), 3.75–4.2 (4H,m; including q at 4.1, J=7Hz), 2.0–2.6 (6H,m), 1.4–1.8 (7H,m; including s at 1.55) and 1.25 (3H, t,J-7Hz)ppm.

A solution of B (2.593 g.) in anhydrous ether (15 ml.) was added dropwise to a stirred suspension of lithium aluminium hydride (297 mg.) in anhydrous ether (60 ml ) cooled to 5° C. The mixture was stirred at 5° C. for a further 1 hour. Water (40 ml.) was then added cautiously. The mixture was separated and the aqueous phase was extracted with ether (4×60 ml.). The combined ethereal phases were dried ($MgSO_4$), and evaporated. The residue was purified by flash chromatography, eluting with 3:2 v/v ethyl acetate/hexane to give 4(E)-6-(2,2-dimethyl-4-phenyl-1,3-dioxan-cis-5-yl)hexenol (C) as an oil (2.22 g.) NMR: 7.1–7.45 (5H,m), 5.0–5.6 (3H,m), 3.95 (2H,q, J=12Hz), 3.05 (2H,t,J=9Hz), 1.8–2.6 (4H,m) and 1.4–1.8 (1OH,m)ppm.

Methanesulphonyl chloride (0.57 ml.) was added dropwise to a stirred solution of triethylamine (1.0 m,.) and C (2.083 g.) in methylene chloride (25 ml. freshly filtered through a short column of basic alumina) cooled to 5° C. The stirred mixture was then allowed to warm up to room temperature during 2 hours. Ether (100 ml.) was then added. The mixture was washed successively with water, and saturated brine, and was then dried (MgSO4) and evaporated. The residue was purified by flash chromatography using 3:2 v/v ethyl acetate/hexane to give 4(E)-6-(2,2-dimethyl-4-phenyl-1,3-dioxan-cis-5-yl)hexenol O-methanesulphonate as an oil (D) (2.176 g.) NMR: 7.3 (5H,s), 5.0–5.55 (3H,m), 4.15 (2H,t,J=6Hz) 3.85 (2H,q, J=12Hz), 2.95 (3H,s) and 1,4–2.65 (13H,m; including 2 s at 1.55)ppm.

Potassium cyanide (405 mg.) was added in portions to a solution of D (1.115 g.) in anhydrous dimethyl sulphoxide (20 ml.) under argon. The mixture was stirred at 75° C. for 2 hours, then diluted with water (15 ml.). The resultant mixture was extracted with ether. The extracts were washed with saturated brine, dried (MgSO4) and evaporated. The residue was purified by flash chromatography using 3:7 v/v ethyl acetate/hexane as eluant to give 5(E)-7-(2,2-dimethyl-4-phenyl-1,3-dioxan-cis-5-yl)heptenonitrile as an oil (687 mg.); NMR: 7.3 (5H,s), 5.0–5.5 (3H,m), 4.0 2H,q,J=11Hz), 1.9–2.5 (5H,m) and 1,3–1.9 (1OH, m, including 2 s at 1.50 )ppm.

EXAMPLE 104

The preparation of an oral dosage form is illustrated by the following tablet formulation:
5(Z)-7-(2,2-diethyl-4-phenyl-1,3-dioxan-cis-5-yl)heptenoic acid (300 parts);
lactose (56 parts);
maize starch (30 parts)
polyvinylpyrrolidone (10 parts); and
magnesium stearate (4 parts)
obtained using a standard wet granulation and compression procedure [all parts by weight]. The lactose may be replaced by an alternative filler such as calcium phosphate, the maize starch by an alternative disintegrant such as calcium carboxymethylcellulose, and the polyvinylpyrrolidone by an alternative binder such as gelatine, if desired.

Similarly the active ingredient may be replaced by another compound of formula I described herein. The tablets may be enteric coated by conventional means, for example to incorporate a coating of cellulose acetate phthalate.

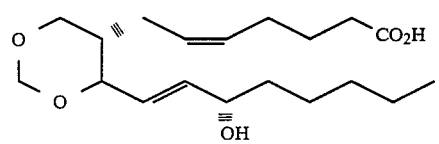

A

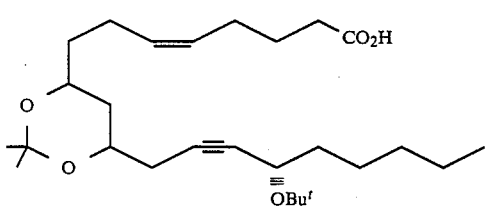

B

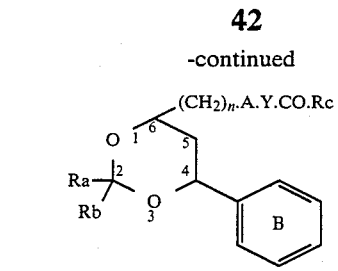

I

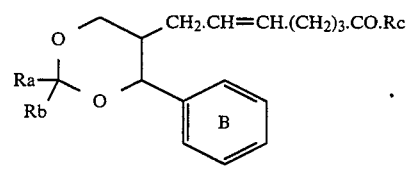

Ia

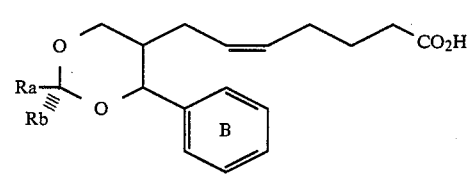

Ib

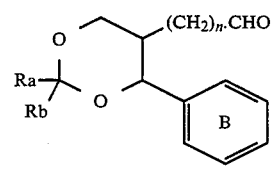

II

III

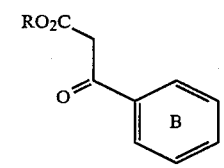

IV

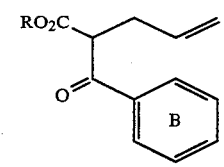

V

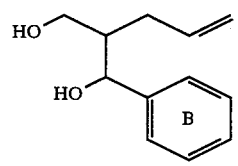

VIa

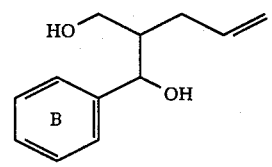

VIb

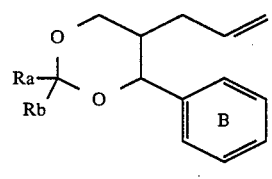

VII

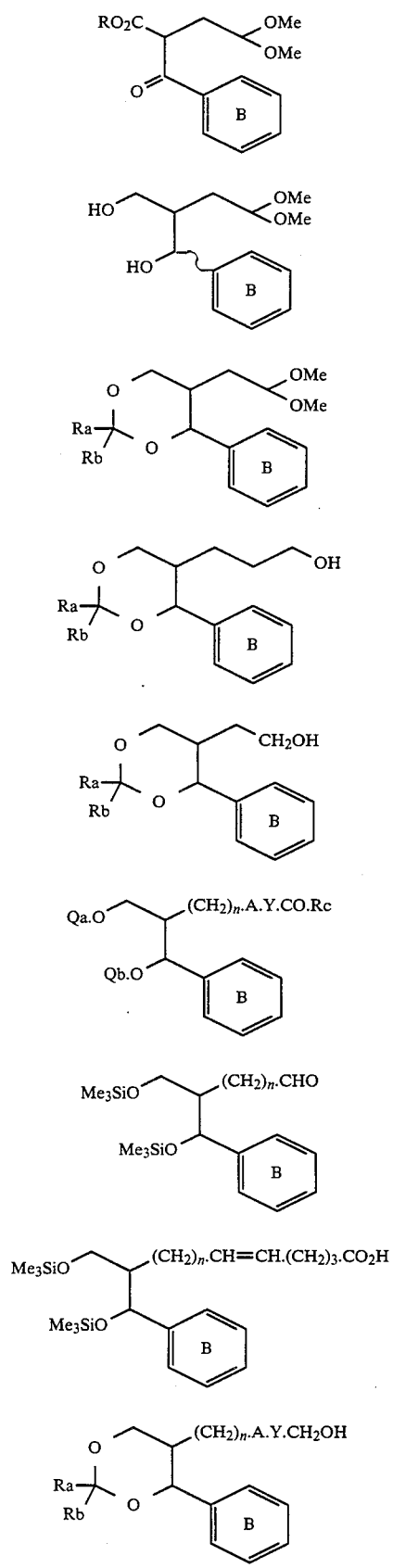

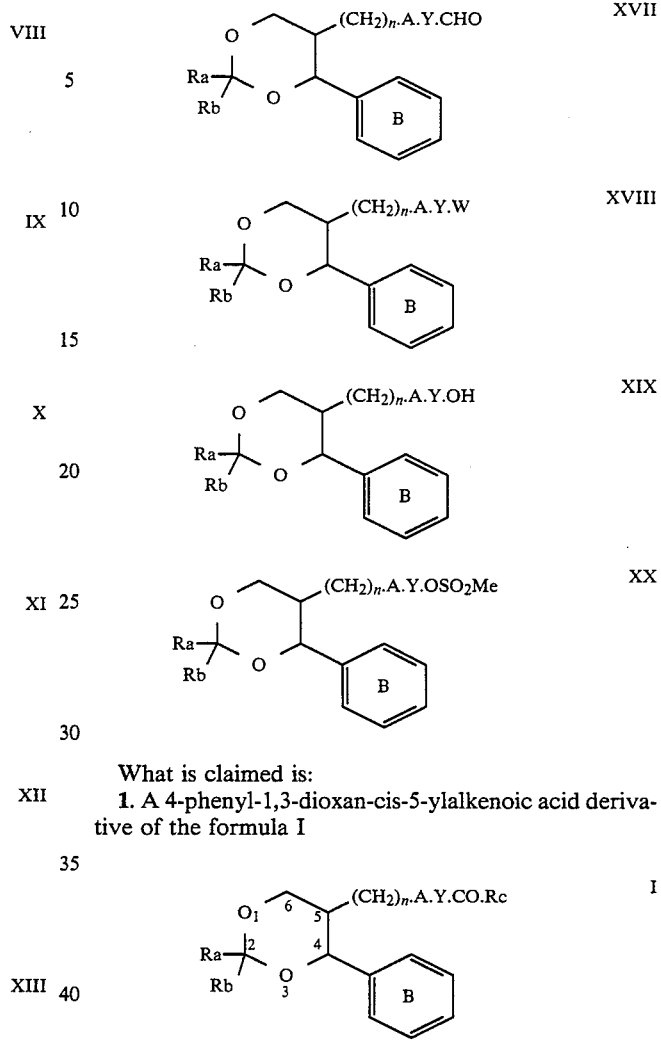

What is claimed is:
1. A 4-phenyl-1,3-dioxan-cis-5-ylalkenoic acid derivative of the formula I

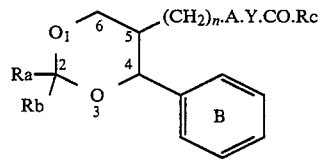

wherein Ra and Rb are independently hydrogen, (2–6C-)alkenyl, (1–8C)alkyl optionally bearing up to three halogeno substituents, independently hydrogen, (2–6C-)alkenyl, (1–8C)alkyl optionally bearing up to three halogeno substituents, pentafluorophenyl, aryl or aryl(-1–4C)alkyl, the latter two of which may optionally bear up to three substituents selected from halogeno, (1–6C)alkyl, (1–6C)alkoxy, (1–6C)alkoxy, (1–4C)alkylenedioxy, trifluoromethyl, cyano, nitro, hydroxy, (2–6C)alkanoyloxy, (1–6C)alkylthio, (1–6C)alkanesulphonyl, (1–6C)alkanoylamino, and oxapolymethylene of 2 to 4 carbon atoms, provided that when both Ra and Rb are alkyl or alkenyl, the total number of carbon atoms in Ra and Rb taken together is 8 or less; or Ra and Rb together form polymethylene of 2 to 7 carbon atoms, optionally bearing one or two (1–4C)alkyl substituents; Rc is hydroxy, (1–6C)alkanesulphonamido; n is the integer 1 or 2; A is ethylene or vinylene; Y is polymethylene of 2 to 5 atoms optionally bearing (1–4C)alkyl as a substituent; benzene ring B optionally bears one or two substituents selected from halogeno, (1–6C)alkyl, (1–6C)alkoxy, hydroxy, (2–6C)alkanoyloxy. (1–6C)alkanoylanino, trifluoromethyl and nitro; and the substituents at positions 4 and 5 of the dioxane ring have cis-relative stereochemistry; or for those compounds wherein Rc is hydroxy, a salt thereof with a base affording a physiologically acceptable cation.

2. A compound as claimed in claim 1 wherein Ra and Rb are, independently, hydrogen, methyl, ethyl, propyl, isopropyl, butyl, pentyl, hexyl, heptyl, octyl. vinyl, allyl, 2-methylallyl, chloromethyl, trifluoromethyl or 2,2,2-trifluoroethyl, pentafluorophenyl, 1-naphthyl, 2-napthyl, benzyl, 1-phenylethyl, 2-phenylethyl or phenyl, the latter six of which may optionally bear up to three substituents selected from: fluoro, chloro, bromo, iodo, methyl, ethyl, propyl, isopropyl, methoxy, ethoxy, propoxy, methylenedioxy, ethylenedioxy, isopropllidenedioxy, trifluoromethyl, cyano, nitro, methylthio, ethylthio, methanesulphonyl, ethanesulphonyl, formamido, acetamido, propionamido, hydroxy, acetoxy, propionyloxy, methyleneoxymethylene and ethyleneoxymethylene; provided that when both Ra and Rb are alkyl or alkenyl, the total number of carbon atoms in Ra and Rb taken together is 8 or less; or Ra and Rb together constitute ethylene, trimethylene, tetramethylene, pentamethylene or hexamethylene, any of which may bear an optional methyl substituent; Rc is hydroxy, methoxy, ethoxy, methanesulphonamido, ethanesulphonamido or 1-methylethanesulphonamido; n is the integer 1 or 2; A is ethylene or vinylene; Y is ethylene, trimethylene or tetramethylene, any of which may optionally bear a methyl substituent; and benzene ring B optionally bears one or two substituents selected from fluoro, chloro, bromo, iodo, methyl, ethyl, isopropyl, propyl, methoxy, ethoxy, propoxy, hydroxy, acetoxy, propionyloxy, formamido, acetamido, propionamido, trifluoromethyl and nitro.

3. A compound as claimed in claim 1 wherein Ra and Rb are, independently, hydrogen, methyl, ethyl, propyl, isopropyl, butyl, pentyl, hexyl, octyl, vinyl, allyl, 2-methylallyl, trifluoromethyl, chloromethyl, 2-chloroethyl, phenyl optionally bearing a fluoro, chloro, bromo, methyl, methoxy, trifluoromethyl, methylthio methanesulphonyl, nitro, hydroxy, cyano, acetamido, methylenedioxy or a methyleneoxymethylene (—CH$_2$OCH$_2$) substituent, dichlorophenyl, dimethylphenyl, pentafluorophenyl, 1-naphthyl, 2-naphthyl or benzyl; or together form trimethylene, pentamethylene or hexamethylene, optionally bearing a methyl substituent; provided that when both Ra and Rb are alkyl or alkenyl the total number of carbon atoms in Ra and Rb taken together is 8 or less; and benzene ring B is phenyl, 2-methylphenyl, 2-ethylphenyl, 2-isopropylphenyl, 2-methoxyphenyl, 2-fluorophenyl, 2-chlorophenyl, 2-bromophenyl, 2-hydroxyphenyl, 2-trifluoromethylphenyl, 3-trifluoromethylphenyl, 3-fluorophenyl, 3-chlorophenyl, 4-fluorophenyl, 4-methylphenyl or 2,6-difluorophenyl.

4. A compound as claimed in claim 1 wherein benzene ring B is unsubstituted; ortho-substituted by fluoro, chloro, methyl, hydroxy, methoxy, ethyl or isopropyl, or meta-substituted by fluoro or chloro.

5. A compound as claimed in claim 1 wherein Rc is hydroxy, methoxy, ethoxy, methanesulphonamido or ethanesulphonamido.

6. A 7-(4-phenyl-1,3-dioxan-cis-5-yl)heptenoic acid derivative of the formula Ia

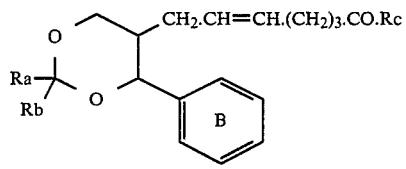

wherein Ra and Rb are:
(i) independently hydrogen or (1–4C)alkyl, optionally bearing 1 to 3 halogeno substituents;
(ii) one of the two is hydrogen or (1–4C)alkyl, and the other is phenyl, naphthyl or phenyl-(1–4C)alkyl, optionally bearing 1 or 2 substituents selected from halogeno, (1–4C)alkyl, (1–4C)alkoxy, (1–4C)alkylenedioxy, trifluoromethyl, cyano, nitro, hydroxy, (2–4C)alkanoyloxy, (1–4C)alkylthio, (1–4C)alkanesulphonyl, (1–4C)alkanoylamino and oxapolymethylene of 2 to 4 carbon atoms, or pentafluorophenyl;
(iii) one of the two is hydrogen and the other is (5–8C)alkyl or (2–6C)alkenyl; or
(iv) both together form polymethylene of 2 to 7 carbon atoms optionally bearing a (1–4C)alkyl substituent;

Rc is hydroxy, (1–4C)alkoxy or (1–4C)alkansulphonamido; and benzene ring B optionally bears a single substituent located at the 2-position selected from halogeno, (1–4C)alkyl, (1–4C)alkoxy, hydroxy, (2–4C) alkanoyloxy, (1–4C)alkanoylamino and trifluoromethyl, or bears a 3-halogeno substituent; and the substituents at positions 4 and 5 of the dioxane ring have cis-relative stereochemistry; or for those compounds wherein Rc is hydroxy, a salt thereof with a base affording a physiologically acceptable cation.

7. A compound as claimed in claim 6 wherein:
(i) Ra and Rb are both hydrogen, methyl, ethyl, Propyl, butyl or trifluoromethyl;
(ii) one of Ra is hydrogen and the other is trifluoromethyl, chloromethyl, benzyl, isoproply, hexyl, octyl, phenyl, (optionally bearing 1 or 2 fluoro, chloro, bromo, methyl, methoxy, trifluoromethyl, hydroxy, cyano, methylthio or acetamido), phenyl bearing methylenedixoy or methyleneoxymethylene (—CH$_2$OCH$_2$), pentafluorophenyl, 1-naphthyl or 2-naphthyl; or
(iii) Ra and Rb together form trimethylene, tetramethylene, pentamethylene, hexamethylene or a group of the formula: —CH$_2$CH$_2$·CHCH$_3$·CH$_2$CH$_2$—; and benzene ring B is phenyl; 2-fluorophenyl, 2-chlorophenyl 2-bromophenyl, 2-methylphenyl, 2-ethylphenyl, 2-isopropylphenyl, 2-methoxyhenyl, 2-hydroxphyenyl, 3-fluorophenyl or 3-chlorophenyl; and Rc is hydroxy, methanesulphonamido or ethanesulphonamido.

8. A 5(Z)-7-(4-phenyl-1,3-dioxan-cis-5-yl)heptenoic acid of the formula Ib

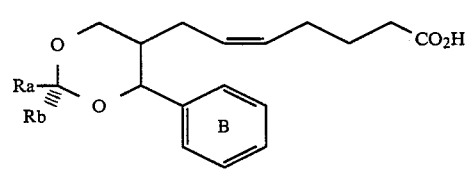

wherein:
(i) Ra and Rb are both hydrogen, methyl, ethyl, propyl, butyl, or trifluoromethyl;
(ii) Ra and Rb together form trimethylene, tetramethylene, pentamethylene, hexamethylene or a group of the formula —CH$_2$CH$_2$·CHCH$_3$·CH$_2$CH$_2$—; or
(iii) Ra is (3–8C)alkyl, trifluoromethyl, chloromethyl, 2-chloroethyl, pentafluorophenyl, or phenyl, benzyl or naphthyl, the last three of which may optionally bear 1 or 2 halogeno, (1–4C) alkyl, (1–4C)alkoxy, trifluoromethyl, hydroxy, cyano, (1–4C)alkylthio or (1–4C)alkanoylamino substituents, or a methylenedioxy or methylene neoxymethylene substituent, and Rb is hydrogen;
benzene ring B is unsubstituted or is 2-halogeno-, 2-(1–4C)alkyl-, 2-(1–4C)alkoxy-, 2-hydroxy- or 3-halogeno-phenyl;
Ra and the substituents at the 4 and 5-positions of the dioxane ring have cis-relative stereochemistry; and the carbon atoms adjacent to the vinylene group have the indicated cis-relative stereochemistry; or a salt thereof with a base affording a physiologically acceptable cation; or a methyl or ethyl ester thereof; or a methanesulphonamido, ethanesulphonamido or 1-methylethanesulphonamido derivative thereof.

9. A compound as claimed in claim 8 wherein Ra and Rb have the meanings defined in (i) and (ii) of claim 8; or Ra is isopropyl, butyl, hexyl, octyl, trifluoromethyl, chloromethyl, 2-chloroethyl, pentafluorophenyl, benzyl, naphthyl or phenyl (optionally bearing 1 or 2 fluoro, chloro, bromo, methyl, methoxy, trifluoromethyl, hydroxy, cyano, methylthio or acetamido substituents, or bearing a methylenedioxy or methyleneoxymethylene substituent), and Rb is hydrogen; and benzene ring B is unsubstituted or bears a 2-fluoro, 2-chloro, 2-bromo, 3-fluoro, 3-chloro, 2-methyl, 2-ethyl, 2-isopropyl, 2-methoxy, or 2-hydroxy substituent.

10. A 5(Z)-7-(4-phenyl-1,3-dioxan-cis-5-yl) heptenoic acid of the formula Ib

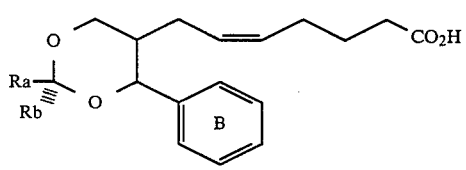

wherein Ra, Rb and benzene ring B are selected from the following combinations:

| No. | Ra | Rb | Benzene Ring B |
|---|---|---|---|
| 1 | methyl | methyl | 3-fluorophenyl |
| 2 | methyl | methyl | 3-chlorophenyl |
| 3 | methyl | methyl | 2-methoxyphenyl |
| 4 | methyl | methyl | 2-methylphenyl |
| 5 | methyl | H | phenyl |
| 6 | trifluoromethyl | H | phenyl |
| 7 | isopropyl | H | phenyl |
| 8 | ethyl | ethyl | phenyl |
| 9 | ethyl | ethyl | 2-fluorophenyl |
| 10 | 2-chlorophenyl | H | phenyl |
| 11 | 2-methylphenyl | H | phenyl |
| 12 | 2-ethylphenyl | H | phenyl |
| 13 | 2-fluorophenyl | H | phenyl |
| 14 | 2-chlorophenyl | H | phenyl |
| 15 | 2-methylthiophenyl | H | phenyl |
| 16 | 4-fluorophenyl | H | phenyl |
| 17 | 4-chlorophenyl | H | phenyl |
| 18 | 4-methoxyphenyl | H | phenyl |
| 19 | 3,4-methylene dioxyphenyl | H | phenyl |
| 20 | 3,4-(methyleneoxymethylene)-phenyl | H | phenyl |
| 21 | methyl | methyl | 2-hydroxyphenyl |

(wherein H stands for hydrogen); and from the following combinations;

| No | Ra + Rb | Benzene Ring B |
|---|---|---|
| 22 | pentamethylene | phenyl |
| 23 | hexamethylene | phenyl |
| 24 | (3-methyl)pentamethylene | phenyl | or a salt thereof with a base affording a physiologically acceptable cation.

11. A salt as claimed in claim 1 which is an alkali metal, alkaline earth metal, aluminium or ammonium salt, or a salt with an organic amine or quaternary base, forming a physiologically acceptable cation.

12. A methanesulphonamido derivative of an acid as claimed in claim 10 or of 5(Z)-7-(2,2-dimethyl-4-phenyl-1,3-dioxan-cis-5-yl)heptenoic acid.

13. A method for antagonising one or more of the actions of thromboxane A$_2$ in a warm-blooded animal requiring such treatment which comprises administering to said animal a thromboxane A$_2$ antagonistically effective amount of a compound of formula I as defined in claim 1, when Rc is hydroxy, a salt of said compound with a base affording a physiologically acceptable cation.

14. A pharmaceutical composition for use in antagonising one or more of the actions thromboxane A$_2$ in a warm-blooded animal requiring such treatment which comprises an antagonistically effective amount of a compound of formula I, or a salt thereof, as claimed in claim 1 together with a pharmaceutically acceptable diluent or carrier.

15. A method for antagonising one or more of the actions of thromboxane A$_2$ in a warm-blooded animal requiring such treatment which comprises administering to said animal an antagonistically effective amount of a thromboxane A$_2$ antagonistically active 4-phenyl-1,3-dioxan-cis-5-ylalkenoic acid derivative.

* * * * *